(12) United States Patent
Thompson et al.

(10) Patent No.: US 9,067,963 B2
(45) Date of Patent: Jun. 30, 2015

(54) N-ALKYL 2-(DISUBSTITUTED)ALKYNYLADENOSINE-5-URONAMIDES AS A₂A AGONISTS

(71) Applicant: Lewis and Clark Pharmaceuticals, Inc., Charlottesville, VA (US)

(72) Inventors: Robert D Thompson, Charlottesville, VA (US); Anthony Beauglehole, Charlottesville, VA (US); Guoquan Wang, Charlottesville, VA (US)

(73) Assignee: Lewis and Clark Pharmaceuticals, LLC, Charlottesville, VA (US)

( * ) Notice: Subject to any disclaimer, the term of this patent is extended or adjusted under 35 U.S.C. 154(b) by 0 days.

(21) Appl. No.: 13/956,111

(22) Filed: Jul. 31, 2013

(65) Prior Publication Data

US 2014/0037538 A1    Feb. 6, 2014

Related U.S. Application Data

(60) Provisional application No. 61/787,188, filed on Mar. 15, 2013, provisional application No. 61/678,605, filed on Aug. 1, 2012.

(51) Int. Cl.
*A61K 51/00* (2006.01)
*A61M 36/14* (2006.01)
*C07H 19/16* (2006.01)

(52) U.S. Cl.
CPC ..................................... *C07H 19/16* (2013.01)

(58) Field of Classification Search
None
See application file for complete search history.

(56) References Cited

U.S. PATENT DOCUMENTS

| | | | |
|---|---|---|---|
| 4,956,345 A | 9/1990 | Miyasaka et al. | |
| 5,189,027 A | 2/1993 | Miyashita et al. | |
| 5,270,304 A | 12/1993 | Kogi et al. | |
| 5,283,327 A | 2/1994 | Yamaguchi et al. | |
| 5,459,254 A | 10/1995 | Yamaguchi et al. | |
| 6,322,771 B1 | 11/2001 | Linden et al. | |
| 6,387,889 B1 | 5/2002 | Endo et al. | |
| 6,914,053 B2 | 7/2005 | Cristalli | |
| 7,214,665 B2 | 5/2007 | Linden et al. | |
| 7,605,143 B2 | 10/2009 | Rieger et al. | |
| 8,058,259 B2 | 11/2011 | Thompson et al. | |
| 8,252,767 B2 | 8/2012 | Thompson et al. | |
| 8,263,762 B2 | 9/2012 | Beauglehole et al. | |
| 8,293,720 B2 | 10/2012 | Thompson et al. | |
| 2004/0121978 A1 | 6/2004 | Cristalli | |
| 2007/0072843 A1* | 3/2007 | Wang et al. | 514/217.06 |
| 2008/0009460 A1 | 1/2008 | Linden et al. | |
| 2008/0027081 A1* | 1/2008 | Savory | 514/263.24 |
| 2008/0312160 A1 | 12/2008 | Guerrant et al. | |

FOREIGN PATENT DOCUMENTS

| | | | |
|---|---|---|---|
| JP | 3025557 B | * | 4/1991 |
| WO | 93/22328 A2 | | 11/1993 |
| WO | 20041022573 A2 | | 3/2004 |
| WO | WO 2008124150 A1 | * | 10/2008 |
| WO | 20081143667 A1 | | 11/2008 |
| WO | WO 2011002917 A1 | * | 1/2011 |

OTHER PUBLICATIONS

Patani et al. Chem. Rev. 1996, 96, 3147-3176.*
Homma et al. J. Med. Chem. 1992, 35, 2881-2890.*
PCT/US2013/053053 International Search Report and Written Opinion, Mailed Dec. 20, 2013 (corresponding PCT application).

* cited by examiner

*Primary Examiner* — Michael G Hartley
*Assistant Examiner* — Sean R Donohue
(74) *Attorney, Agent, or Firm* — Vance Intellectual Property, PC

(57) ABSTRACT

The present invention provides N-alkyl 2-(disubstituted) alkynyladenosine-5'-uronamides and derivatives thereof and pharmaceutical compositions containing the same that are selective agonists of $A_{2A}$ adenosine receptors (ARs). These compounds and compositions are useful as pharmaceutical agents.

18 Claims, No Drawings

N-ALKYL 2-(DISUBSTITUTED)ALKYNYLADENOSINE-5'-URONAMIDES AS $A_2A$ AGONISTS

FIELD OF THE INVENTION

The present invention relates to N-Alkyl 2-(disubstituted) alkynyladenosine-5'-uronamides and pharmaceutical compositions that are selective agonists of $A_{2A}$ adenosine receptors (ARs). These compounds and compositions are useful as pharmaceutical agents.

BACKGROUND OF THE INVENTION

Adenosine $A_{2A}$ receptors (also known as ADORA2A) are members of the G protein-coupled receptor (GPCR) family which possess seven transmembrane alpha helices. The receptor is mediated by G proteins, which activate adenylyl cyclase and is abundant in basal ganglia, vasculature and platelets and is a major target of caffeine. The $A_{2A}$ receptor is responsible for regulating myocardial blood flow by vasodilating the coronary arteries, which increases blood flow to the myocardium, but may lead to hypotension. The $A_{2A}$ receptor is also expressed in the brain, where it has important roles in the regulation of glutamate and dopamine release. The $A_{2A}$ receptor signals in both the periphery and the CNS, with agonists explored as anti-inflammatory drugs and antagonists as useful in neurodegenerative disorders such as Parkinson's disease.

Despite the increasing development of adenosine $A_{2A}$ receptor agonists, as described above, only one, regadenoson, an adenosine analog, has been approved for use in the United States as a coronary vasodilator. Typical issues involved with administration of these compounds include side effects due to the wide distribution of adenosine receptors, low brain penetration (which is important for the targeting of CNS diseases), short half-life of compounds, and/or a lack of effects, in some cases possibly due to receptor desensitization or too low receptor density in the targeted tissue. Therefore, it is important to continue to synthesize and test additional $A_{2A}$ receptor agonists in order to develop new and improved therapeutic agents.

SUMMARY OF THE INVENTION

Accordingly, in an aspect, the present invention provides novel N-alkyl 2-(disubstituted)alkynyladenosine-5'-uronamides or pharmaceutically acceptable salts thereof that are $A_{2A}$ agonists.

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides methods of treating a pathological condition or symptom in a mammal for which the $A_{2A}$ receptor is implicated (e.g., an adenosine $A_{2A}$ receptor associated state, such as glaucoma or ocular hypertension) and agonism of the receptor provides therapeutic benefit by administering to a subject an effective amount of an adenosine $A_{2A}$ receptor agonist of the present invention or a pharmaceutically acceptable salt thereof.

In another aspect, the present invention provides methods of treating and/or preventing an adenosine $A_{2A}$ receptor-associated state in a subject by administering to the subject an effective amount of an adenosine $A_{2A}$ receptor agonist of the present invention or a pharmaceutically acceptable salt thereof.

In another aspect, the present invention provides adenosine $A_{2A}$ receptor agonists for use in medical therapy.

In another aspect, the present invention provides the use of adenosine $A_{2A}$ receptor agonists of the present invention for the manufacture of a medicament for the treatment of a pathological condition or symptom in a mammal for which the $A_{2A}$ receptor is implicated (e.g., an adenosine $A_{2A}$ receptor associated state, such as glaucoma or ocular hypertension) and agonism of the receptor provides therapeutic benefit.

These and other objects, which will become apparent during the following detailed description, have been achieved by the inventors' discovery that the presently claimed compounds or pharmaceutically acceptable salt forms thereof are expected to be effective $A_{2A}$ agonists.

DETAILED DESCRIPTION OF THE INVENTION

All references cited herein are hereby incorporated in their entirety herein by reference.

In an aspect, the present invention provides novel compounds of Formula I or a stereoisomer or pharmaceutically acceptable salt thereof:

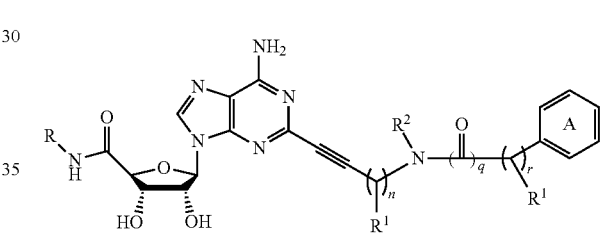

I wherein:
R is selected from: $C_{1-8}$ alkyl and $C_{3-8}$ cycloalkyl;
$R^1$ is independently selected from: H, $C_{1-8}$ alkyl, and $C_{3-8}$ cycloalkyl;
q is 1;
r is independently selected from 0, 1, 2, 3, 4 and 5;
$R^2$ is selected from: H, $C_{1-8}$ alkyl, $C_{3-8}$ cycloalkyl-$C_{0-8}$ alkylene-, $C_{1-8}$ alkoxy-$C_{1-8}$ alkylene-, 5-10 membered heterocyclyl-$C_{0-8}$ alkylene-, 5-10 membered heteroaryl-$C_{0-8}$ alkylene-, and aryl-$C_{0-8}$ alkylene-;
alternatively, q is 0, r is 1, and $R^2$ is —C(O)—$R^{2A}$;
$R^{2A}$ is selected from: $C_{1-8}$ alkyl, $C_{3-8}$ cycloalkyl-$C_{0-8}$ alkylene-, $C_{1-8}$ alkoxy-$C_{1-8}$ alkylene-, 5-10 membered heterocyclyl-$C_{0-8}$ alkylene-, 5-10 membered heteroaryl-$C_{0-8}$ alkylene-, and aryl-$C_{0-8}$ alkylene-;
ring A is a phenyl ring or a 5-6 membered heteroaryl attached via the carbon atom shown and having 1-3 ring heteroatoms selected from O, N, and $S(O)_p$;
ring A is optionally substituted with 1-3 $R^3$ groups;
$R^3$ is independently selected from: $C_{1-8}$ alkyl, F, Cl, Br, I, —CN, $OR^a$, $SR^a$, $NR^aR^b$, $CF_3$, $OCF_3$, $COR^a$, $CO_2R^a$, C(O)$NR^aR^b$, OC(O)$R^a$, $OCO_2R^a$, OC(O)$NR^aR^b$, $NR^bCOR^a$, $NR^bCO_2R^a$, $NR^bC(O)NR^aR^b$, $S(O)_pNR^aR^b$, $C_{3-10}$ cycloalkyl-$C_{0-8}$ alkylene-, 5-10 membered heterocyclyl-$C_{0-8}$ alkylene-, aryloxy, aryl-$C_{0-8}$ alkylene-, and 5-10 membered heteroaryl-$C_{0-8}$ alkylene-;
$R^a$ is independently selected from: H, $C_{1-8}$ alkyl and $C_{3-8}$ cycloalkyl-$C_{0-8}$ alkylene-;

$R^b$ is independently selected from: H, $C_{1-8}$ alkyl and $C_{3-8}$ cycloalkyl-$C_{0-8}$ alkylene-;

n is independently selected from: 1, 2, 3, 4, 5, and 6; and, p is independently selected from: 0, 1, and 2.

In another aspect, the present invention provides a novel compound of Formula Ia, or a stereoisomer or pharmaceutically acceptable salt thereof, wherein:

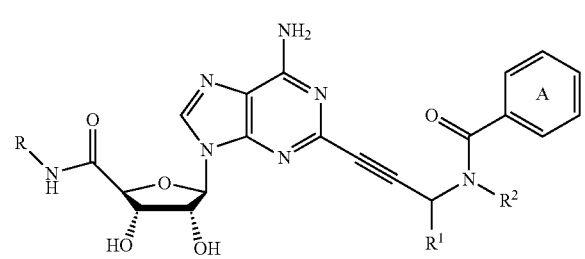

Ia wherein:

R is selected from: $C_{1-4}$ alkyl and $C_{3-6}$ cycloalkyl;

$R^1$ is selected from: H and $C_{1-4}$ alkyl;

$R^2$ is selected from: H, $C_{1-4}$ alkyl, $C_{3-6}$ cycloalkyl-$C_{0-2}$ alkylene-, and $C_{1-4}$ alkoxy-$C_{1-4}$ alkylene-;

ring A is selected from phenyl, pyridyl, thienyl, furanyl, pyrrolyl, oxazolyl, isoxazolyl, thiazolyl, isothiazolyl, pyrimidyl, and pyridazinyl;

ring A is optionally substituted with 1-2 $R^3$ groups;

$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;

$R^a$ is independently selected from: H, $C_{1-4}$ alkyl and $C_{3-8}$ cycloalkyl-$C_{0-8}$ alkylene-;

$R^b$ is independently selected from: H, $C_{1-4}$ alkyl and $C_{3-8}$ cycloalkyl-$C_{0-8}$ alkylene-; and, p is independently selected from: 0, 1, and 2.

In another aspect, the present invention provides a novel compound of Formula Ia, or a stereoisomer or pharmaceutically acceptable salt thereof, wherein:

R is selected from: methyl, ethyl, and cyclopropyl;

$R^1$ is H;

$R^2$ is selected from: H, methyl, ethyl, isopropyl, isobutyl, cyclopropyl, cyclopropyl-methylene, cyclobutyl, cyclobutyl-methylene, cyclopentyl, and methoxy-ethylene;

ring A is selected from: phenyl, pyridyl, and thienyl;

ring A is optionally substituted with 1-2 $R^3$ groups;

$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;

$R^a$ is independently selected from: H and $C_{1-4}$ alkyl;

$R^b$ is independently selected from: H and $C_{1-4}$ alkyl; and, p is independently selected from: 0, 1, and 2.

In another aspect, the present invention provides a novel compound of Formula Ia, or a stereoisomer or pharmaceutically acceptable salt thereof, wherein:

R is selected from: methyl, ethyl, and cyclopropyl;

$R^1$ is H;

$R^2$ is selected from: methyl, isobutyl, cyclopropyl, cyclopropyl-methylene, cyclobutyl, cyclopentyl, and methoxy-ethylene;

ring A is selected from: phenyl, pyridyl, and thienyl;

ring A is optionally substituted with 1-2 $R^3$ groups;

$R^3$ is independently selected from: $C_{1-4}$ alkyl, F, Cl, —CN, $OR^a$, $CF_3$, and $OCF_3$;

$R^a$ is independently selected from: H and $C_{1-4}$ alkyl; and, $R^b$ is independently selected from: H and $C_{1-4}$ alkyl.

In another aspect, the present invention provides a novel compound of Formula Ia, or a stereoisomer or pharmaceutically acceptable salt thereof, wherein:

R is selected from: methyl, ethyl, and cyclopropyl;

$R^1$ is H;

$R^2$ is selected from: methyl, isobutyl, cyclopropyl, cyclopropyl-methylene, cyclobutyl, cyclopentyl, and methoxy-ethylene;

ring A is phenyl optionally substituted with 1-2 $R^3$ groups;

$R^3$ is independently selected from: $CH_3$, F, Cl, —CN, $CF_3$, and $OCF_3$.

In another aspect, the present invention provides a novel compound of Formula Ia, or a stereoisomer or pharmaceutically acceptable salt thereof, wherein:

R is selected from: methyl, ethyl, and cyclopropyl;

$R^1$ is H;

$R^2$ is selected from: methyl, isobutyl, cyclopropyl, cyclopropyl-methylene, cyclobutyl, cyclopentyl, and methoxy-ethylene;

ring A is 3-pyridyl optionally substituted with 1-2 $R^3$ groups;

$R^3$ is independently selected from: $CH_3$, F, Cl, —CN, $CF_3$, and $OCF_3$.

In another aspect, the present invention provides a novel compound of Formula Ia, or a stereoisomer or pharmaceutically acceptable salt thereof, wherein:

R is selected from: methyl, ethyl, and cyclopropyl;

$R^1$ is H;

$R^2$ is selected from: methyl, isobutyl, cyclopropyl, cyclopropyl-methylene, cyclobutyl, cyclopentyl, and methoxy-ethylene;

ring A is 4-pyridyl optionally substituted with 1-2 $R^3$ groups;

$R^3$ is independently selected from: $CH_3$, F, Cl, —CN, $CF_3$, and $OCF_3$.

In another aspect, the present invention provides a novel compound of Formula Ia, or a stereoisomer or pharmaceutically acceptable salt thereof, wherein:

R is selected from: methyl, ethyl, and cyclopropyl;

$R^1$ is H;

$R^2$ is selected from: methyl, isobutyl, cyclopropyl, cyclopropyl-methylene, cyclobutyl, cyclopentyl, and methoxy-ethylene;

ring A is 2-thienyl optionally substituted with 1-2 $R^3$ groups;

$R^3$ is independently selected from: $CH_3$, F, Cl, —CN, $CF_3$, and $OCF_3$.

In another aspect, the present invention provides a novel compound of Formula I, or a stereoisomer or pharmaceutically acceptable salt thereof, wherein: the compound is selected from a compound of Table 1.

In another aspect, the present invention provides a novel compound of Formula Ib, or a stereoisomer or pharmaceutically acceptable salt thereof:

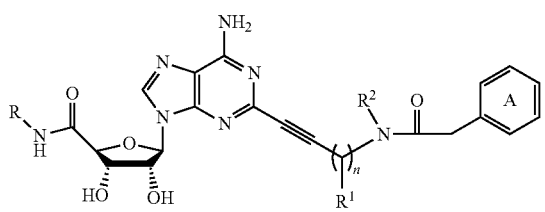

wherein:
R is selected from: $C_{1-4}$ alkyl and $C_{3-6}$ cycloalkyl;
$R^1$ is selected from: H and $C_{1-4}$ alkyl;
$R^2$ is selected from: H, $C_{1-4}$ alkyl, $C_{3-6}$ cycloalkyl-$C_{0-2}$ alkylene-, and $C_{1-4}$ alkoxy-$C_{1-4}$ alkylene-;
ring A is selected from phenyl, pyridyl, thienyl, furanyl, pyrrolyl, oxazolyl, isoxazolyl, thiazolyl, isothiazolyl, pyrimidyl, and pyridazinyl;
ring A is optionally substituted with 1-2 $R^3$ groups;
$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;
$R^a$ is independently selected from: H, $C_{1-4}$ alkyl and $C_{3-8}$ cycloalkyl-$C_{0-8}$ alkylene-;
$R^b$ is independently selected from: H, $C_{1-4}$ alkyl and $C_{3-8}$ cycloalkyl-$C_{0-8}$ alkylene-; and,
p is independently selected from: 0, 1, and 2.

In another aspect, the present invention provides a novel compound of Formula Ib, or a stereoisomer or pharmaceutically acceptable salt thereof, wherein:
R is selected from: methyl, ethyl, and cyclopropyl;
$R^1$ is H;
$R^2$ is selected from: H, methyl, ethyl, isopropyl, isobutyl, cyclopropyl, cyclopropyl-methylene, cyclobutyl, cyclobutyl-methylene, cyclopentyl, and methoxy-ethylene;
ring A is selected from: phenyl, pyridyl, and thienyl;
ring A is optionally substituted with 1-2 $R^3$ groups;
$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;
$R^a$ is independently selected from: H and $C_{1-4}$ alkyl;
$R^b$ is independently selected from: H and $C_{1-4}$ alkyl; and,
p is independently selected from: 0, 1, and 2.

In another aspect, the present invention provides a novel compound of Formula Ib, or a stereoisomer or pharmaceutically acceptable salt thereof, wherein:
R is selected from: methyl, ethyl, and cyclopropyl;
$R^1$ is H;
$R^2$ is selected from: methyl, isobutyl, cyclopropyl, cyclopropyl-methylene, cyclobutyl, cyclopentyl, and methoxy-ethylene;
ring A is selected from: phenyl, pyridyl, and thienyl;
ring A is optionally substituted with 1-2 $R^3$ groups;
$R^3$ is independently selected from: $C_{1-4}$ alkyl, F, Cl, —CN, $OR^a$, $CF_3$, and $OCF_3$;
$R^a$ is independently selected from: H and $C_{1-4}$ alkyl; and,
$R^b$ is independently selected from: H and $C_{1-4}$ alkyl.

In another aspect, the present invention provides a novel compound of Formula Ib, or a stereoisomer or pharmaceutically acceptable salt thereof, wherein:
R is selected from: methyl, ethyl, and cyclopropyl;
$R^1$ is H;
$R^2$ is selected from: methyl, isobutyl, cyclopropyl, cyclopropyl-methylene, cyclobutyl, cyclopentyl, and methoxy-ethylene;
ring A is phenyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula Ib, or a stereoisomer or pharmaceutically acceptable salt thereof, wherein:
R is selected from: methyl, ethyl, and cyclopropyl;
$R^1$ is H;
$R^2$ is selected from: methyl, isobutyl, cyclopropyl, cyclopropyl-methylene, cyclobutyl, cyclopentyl, and methoxy-ethylene;
ring A is 3-pyridyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula Ib, or a stereoisomer or pharmaceutically acceptable salt thereof, wherein:
R is selected from: methyl, ethyl, and cyclopropyl;
$R^1$ is H;
$R^2$ is selected from: methyl, isobutyl, cyclopropyl, cyclopropyl-methylene, cyclobutyl, cyclopentyl, and methoxy-ethylene;
ring A is 4-pyridyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula Ib, or a stereoisomer or pharmaceutically acceptable salt thereof, wherein:
R is selected from: methyl, ethyl, and cyclopropyl;
$R^1$ is H;
$R^2$ is selected from: methyl, isobutyl, cyclopropyl, cyclopropyl-methylene, cyclobutyl, cyclopentyl, and methoxy-ethylene;
ring A is 2-thienyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula Ic, or a stereoisomer or pharmaceutically acceptable salt thereof:

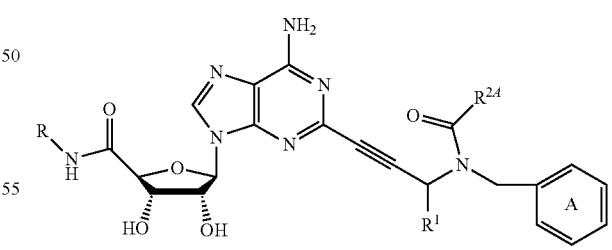

wherein:
R is selected from: $C_{1-4}$ alkyl and $C_{3-6}$ cycloalkyl;
$R^1$ is selected from: H and $C_{1-4}$ alkyl;
$R^{2A}$ is selected from: $C_{1-4}$ alkyl, $C_{3-6}$ cycloalkyl-$C_{0-2}$ alkylene-, and $C_{1-4}$ alkoxy-$C_{1-4}$ alkylene-;
ring A is selected from phenyl, pyridyl, thienyl, furanyl, pyrrolyl, oxazolyl, isoxazolyl, thiazolyl, isothiazolyl, pyrimidyl, and pyridazinyl;

ring A is optionally substituted with 1-2 $R^3$ groups;

$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;

$R^a$ is independently selected from: H, $C_{1-4}$ alkyl and $C_{3-8}$ cycloalkyl-$C_{0-8}$ alkylene-;

$R^b$ is independently selected from: H, $C_{1-4}$ alkyl and $C_{3-8}$ cycloalkyl-$C_{0-8}$ alkylene-; and, p is independently selected from: 0, 1, and 2.

In another aspect, the present invention provides a novel compound of Formula Ic, or a stereoisomer or pharmaceutically acceptable salt thereof, wherein:

R is selected from: methyl, ethyl, and cyclopropyl;
$R^1$ is H;
$R^{2A}$ is selected from: methyl, ethyl, isopropyl, isobutyl, cyclopropyl, cyclopropyl-methylene, cyclobutyl, cyclobutyl-methylene, cyclopentyl, and methoxy-ethylene;
ring A is selected from: phenyl, pyridyl, and thienyl;
ring A is optionally substituted with 1-2 $R^3$ groups;
$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;
$R^a$ is independently selected from: H and $C_{1-4}$ alkyl;
$R^b$ is independently selected from: H and $C_{1-4}$ alkyl; and,
p is independently selected from: 0, 1, and 2.

In another aspect, the present invention provides a novel compound of Formula Ic, or a stereoisomer or pharmaceutically acceptable salt thereof, wherein:

R is selected from: methyl, ethyl, and cyclopropyl;
$R^1$ is H;
$R^{2A}$ is selected from: methyl, isobutyl, cyclopropyl, cyclopropyl-methylene, cyclobutyl, cyclopentyl, and methoxy-ethylene;
ring A is selected from: phenyl, pyridyl, and thienyl;
ring A is optionally substituted with 1-2 $R^3$ groups;
$R^3$ is independently selected from: $C_{1-4}$ alkyl, F, Cl, —CN, $OR^a$, $CF_3$, and $OCF_3$;
$R^a$ is independently selected from: H and $C_{1-4}$ alkyl; and,
$R^b$ is independently selected from: H and $C_{1-4}$ alkyl.

In another aspect, the present invention provides a novel compound of Formula Ic, or a stereoisomer or pharmaceutically acceptable salt thereof, wherein:

R is selected from: methyl, ethyl, and cyclopropyl;
$R^1$ is H;
$R^{2A}$ is selected from: methyl, isobutyl, cyclopropyl, cyclopropyl-methylene, cyclobutyl, cyclopentyl, and methoxy-ethylene;
ring A is phenyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula Ic, or a stereoisomer or pharmaceutically acceptable salt thereof, wherein:

R is selected from: methyl, ethyl, and cyclopropyl;
$R^1$ is H;
$R^{2A}$ is selected from: methyl, isobutyl, cyclopropyl, cyclopropyl-methylene, cyclobutyl, cyclopentyl, and methoxy-ethylene;
ring A is 3-pyridyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula Ic, or a stereoisomer or pharmaceutically acceptable salt thereof, wherein:

R is selected from: methyl, ethyl, and cyclopropyl;
$R^1$ is H;
$R^{2A}$ is selected from: methyl, isobutyl, cyclopropyl, cyclopropyl-methylene, cyclobutyl, cyclopentyl, and methoxy-ethylene;
ring A is 4-pyridyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula Ic, or a stereoisomer or pharmaceutically acceptable salt thereof, wherein:

R is selected from: methyl, ethyl, and cyclopropyl;
$R^1$ is H;
$R^{2A}$ is selected from: methyl, isobutyl, cyclopropyl, cyclopropyl-methylene, cyclobutyl, cyclopentyl, and methoxy-ethylene;
ring A is 2-thienyl optionally substituted with 1-2 $R^3$ groups;
$R^3$ is independently selected from: $CH_3$, F, Cl, —CN, $CF_3$, and $OCF_3$.

In another aspect, the present invention provides a novel compound of Formula I, or a stereoisomer or pharmaceutically acceptable salt thereof, wherein:

R is selected from: $C_{1-4}$ alkyl and $C_{3-6}$ cycloalkyl.

In another aspect, the present invention provides a novel compound of Formula I, or a stereoisomer or pharmaceutically acceptable salt thereof, wherein:

R is selected from: methyl, ethyl, and cyclopropyl.

In another aspect, the present invention provides a novel compound of Formula I, or a stereoisomer or pharmaceutically acceptable salt thereof, wherein:

$R^1$ is selected from: H and $C_{1-4}$ alkyl.

In another aspect, the present invention provides a novel compound of Formula I, or a stereoisomer or pharmaceutically acceptable salt thereof, wherein:

$R^1$ is H.

In another aspect, the present invention provides a novel compound of Formula I, or a stereoisomer or pharmaceutically acceptable salt thereof, wherein:

$R^2$ is selected from: H, $C_{1-4}$ alkyl, $C_{3-6}$ cycloalkyl-$C_{0-2}$ alkylene-, and $C_{1-4}$ alkoxy-$C_{1-4}$ alkylene-.

In another aspect, the present invention provides a novel compound of Formula I, or a stereoisomer or pharmaceutically acceptable salt thereof, wherein:

$R^2$ is selected from: H, methyl, ethyl, isopropyl, isobutyl, cyclopropyl, cyclopropyl-methylene, cyclobutyl, cyclobutyl-methylene, cyclopentyl, and methoxy-ethylene.

In another aspect, the present invention provides a novel compound of Formula I, or a stereoisomer or pharmaceutically acceptable salt thereof, wherein:

$R^2$ is selected from: methyl, isobutyl, cyclopropyl, cyclopropyl-methylene, cyclobutyl, cyclopentyl, and methoxy-ethylene.

In another aspect, the present invention provides a novel compound of Formula I, or a stereoisomer or pharmaceutically acceptable salt thereof, wherein:

ring A is selected from phenyl, pyridyl, thienyl, furanyl, pyrrolyl, oxazolyl, isoxazolyl, thiazolyl, isothiazolyl, pyrimidyl, and pyridazinyl; and,
ring A is optionally substituted with 1-2 $R^3$ groups.

In another aspect, the present invention provides a novel compound of Formula I, or a stereoisomer or pharmaceutically acceptable salt thereof, wherein:

ring A is selected from: phenyl, pyridyl, and thienyl; and,
ring A is optionally substituted with 1-2 $R^3$ groups.

In another aspect, the present invention provides a novel compound of Formula I, or a stereoisomer or pharmaceutically acceptable salt thereof, wherein:

ring A is phenyl optionally substituted with 1-2 $R^3$ groups.

In another aspect, the present invention provides a novel compound of Formula I, or a stereoisomer or pharmaceutically acceptable salt thereof, wherein:
ring A is 3-pyridyl optionally substituted with 1-2 $R^3$ groups.

In another aspect, the present invention provides a novel compound of Formula I, or a stereoisomer or pharmaceutically acceptable salt thereof, wherein:
ring A is 4-pyridyl optionally substituted with 1-2 $R^3$ groups.

In another aspect, the present invention provides a novel compound of Formula I, or a stereoisomer or pharmaceutically acceptable salt thereof, wherein:
ring A is 2-thienyl optionally substituted with 1-2 $R^3$ groups.

In another aspect, the present invention provides a novel compound of Formula I, or a stereoisomer or pharmaceutically acceptable salt thereof, wherein:
$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;
$R^a$ is independently selected from: H, $C_{1-4}$ alkyl and $C_{3-8}$ cycloalkyl-$C_{0-8}$ alkylene-; and,
$R^b$ is independently selected from: H, $C_{1-4}$ alkyl and $C_{3-8}$ cycloalkyl-$C_{0-8}$ alkylene-.

In another aspect, the present invention provides a novel compound of Formula I, or a stereoisomer or pharmaceutically acceptable salt thereof, wherein:
$R^3$ is independently selected from: $C_{1-4}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;
$R^a$ is independently selected from: H and $C_{1-4}$ alkyl; and,
$R^b$ is independently selected from: H and $C_{1-4}$ alkyl.

In another aspect, the present invention provides a novel compound of Formula I, or a stereoisomer or pharmaceutically acceptable salt thereof, wherein:
$R^3$ is independently selected from: $C_{1-4}$ alkyl, F, Cl, —CN, $OR^a$, $CF_3$, and $OCF_3$;
$R^a$ is independently selected from: H and $C_{1-4}$ alkyl; and,
$R^b$ is independently selected from: H and $C_{1-4}$ alkyl.

In another aspect, the present invention provides a novel compound of Formula I, or a stereoisomer or pharmaceutically acceptable salt thereof, wherein:
$R^3$ is independently selected from: $CH_3$, F, Cl, —CN, $CF_3$, and $OCF_3$.

In another aspect, the present invention provides a novel compound of Formula I, or a stereoisomer or pharmaceutically acceptable salt thereof, wherein: n is independently selected from: 1 and 2.

In another aspect, the present invention provides a novel compound of Formula I, or a stereoisomer or pharmaceutically acceptable salt thereof, wherein: n is 1.

In another aspect, the present invention provides a novel compound of Formula I, or a stereoisomer or pharmaceutically acceptable salt thereof, wherein: one or more H are replaced by D. For example, $R^1$ can be D, $R^2$ can be D, ring A can be partially or fully substituted with D, the adenosine-uronamide hydrogens can be partially or fully replaced by D. In addition, the groups recited in R, $R^1$, $R^2$, $R^{2A}$, $R^3$, $R^a$, and $R^b$ that contain a hydrogen (e.g., alkyl, cycloalkyl, alkylene, carbocycle, aryl, heterocycle, and heteroaryl) can be partially or fully replaced by D (e.g., $CD_3$, $CD_2CD_3$, $CD_2CD(CD_3)_2$, $d_5$-cyclopropyl, $d_7$-cyclobutyl, $d_9$-cyclopentyl, $d_5$-cyclopropyl-$CD_2$, $d_5$-phenyl, $d_4$-phenyl (one $R^3$ is present), $d_3$-phenyl (two $R^3$ are present), $d_4$-pyridyl, $d_3$-pyridyl (one $R^3$ is present), and $d_2$-pyridyl (two $R^3$ are present).

In another aspect, the present invention provides a novel compound of Formula I, wherein the compound is a deuterium-enriched compound of $I_1$-$I_{10}$ or a stereoisomer or pharmaceutically acceptable salt thereof:

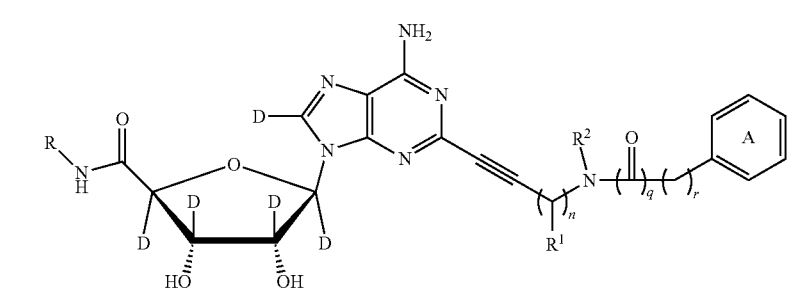

$I_1$

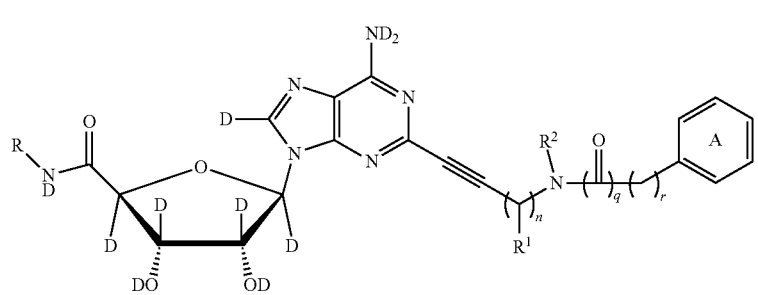

$I_2$

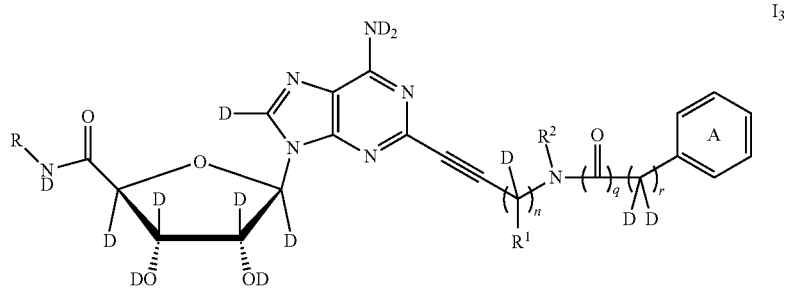
I₃
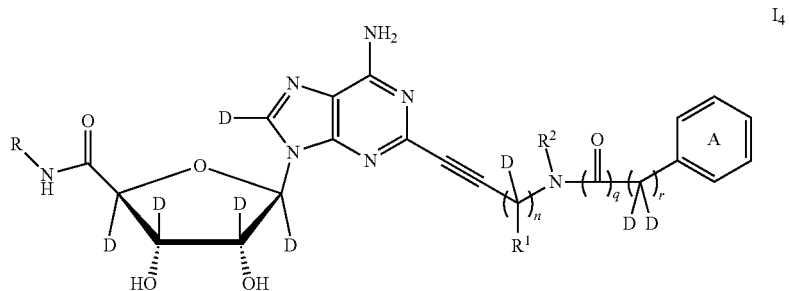
I₄
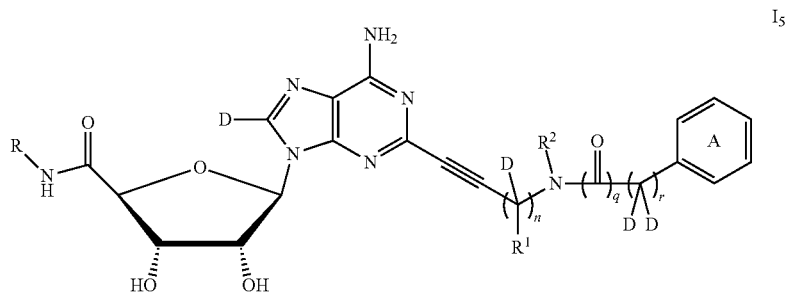
I₅
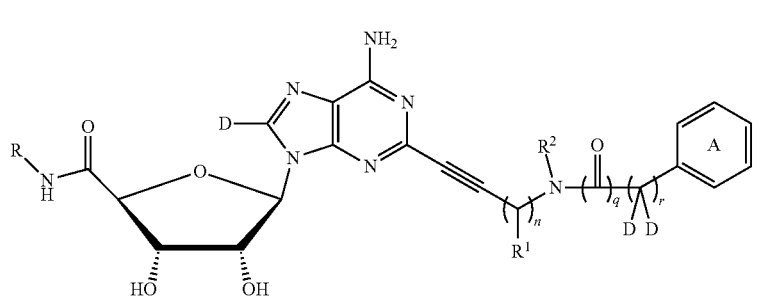
I₆
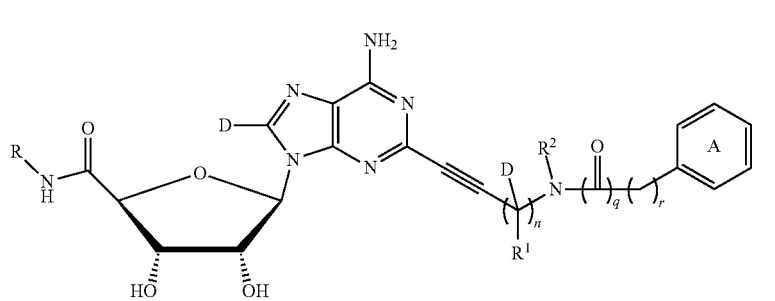
I₇

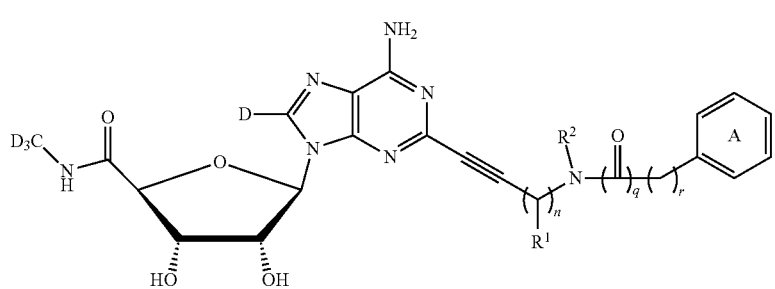

I₈

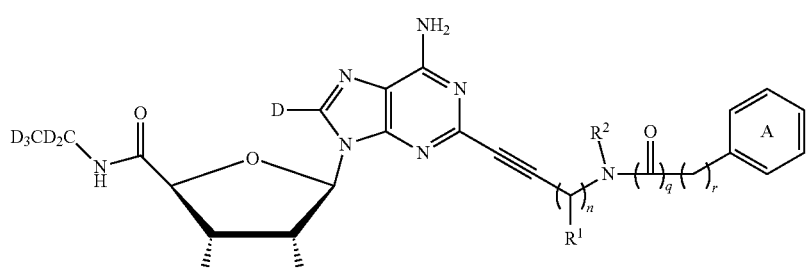

I₉

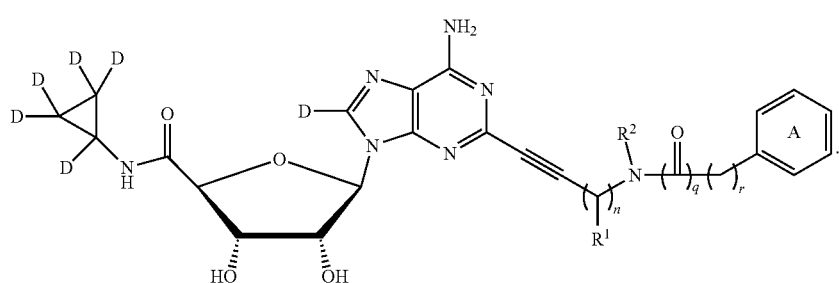

I₁₀

Deuterium-enriched compounds of the present invention can be prepared by a number of known methods including deuterium exchange of acid labile hydrogens (e.g., contacting the compound with NaOD in $D_2O$) and using deuterated starting materials (e.g., deuterated iodo-adenosine-uronamide.

In another aspect, the present invention provides novel pharmaceutical compositions, comprising: a pharmaceutically acceptable carrier and a therapeutically effective amount of a compound of the present invention or a pharmaceutically acceptable salt form thereof.

In another aspect, the pharmaceutical composition further comprises an anti-inflammatory compound. Examples of anti-inflammatory compounds include a Type IV phosphodiesterase (PDE) inhibitor or another anti-inflammatory compound (e.g., other than a PDE inhibitor). The Type IV phosphodiesterase inhibitor may be, for example, rolipram, cilomilast, roflumilast, mesembrine, ibudilast, ONO6126, AWD12281, IC485, CP671305, HT0712, or GRC3886.

The present invention further provides novel pharmaceutical compositions that include an adenosine $A_{2A}$ agonist in combination with one of more members selected from: (a) Leukotriene biosynthesis inhibitors, 5-lipoxygenase (5-LO) inhibitors, and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2-alkylsulfonamides of Formula (5.2.8); 2,6-di-tert-butylphenol hydrazones of Formula (5.2.10); Zeneca ZD-2138 of Formula (5.2.11); SB-210661 of Formula (5.2.12); pyridinyl-substituted 2-cyanonaphthalene compound L-739,010; 2-cyanoquinoline compound L-746,530; indole and quinoline compounds MK-591, MK-886, and BAY x 1005; (b) Receptor antagonists for leukotrienes LTB4, LTC4, LTD4, and LTE4 selected from the group consisting of phenothiazin-3-one compound L-651,392; amidino compound CGS-25019c; benzoxazolamine compound ontazolast; benzenecarboximidamide compound BIIL 284/260; compounds zafirlukast, ablukast, montelukast, pranlukast, verlukast (MK-679), RG-12525, Ro-245913, iralukast (CGP 45715A), and BAY x 7195; (c) 5-Lipoxygenase (5-LO) inhibitors; and 5-lipoxygenase activating protein (FLAP) antagonists; (d) Dual inhibitors of 5-lipoxygenase (5-LO) and antagonists of platelet activating factor (PAF); (e) Theophylline and aminophylline; (f) COX-1 inhibitors (NSAIDs); and nitric oxide NSAIDs; (g) COX-2 selective inhibitor rofecoxib; (h) Inhaled glucocorticoids with reduced systemic side effects selected from the group consisting of prednisone, prednisolone, flunisolide, triamcinolone acetonide, beclomethasonedipropionate, budesonide, fluticasone propionate, and mometasonefuroate; (i) Platelet activating factor (PAF) antagonists; (j) Monoclonal antibodies active against endogenous inflammatory entities; (k) Anti-tumor necrosis factor (TNFα) agents selected from the group consisting of etanercept, infliximab, and D2E7; (l) Adhesion molecule inhibitors including VLA-4 antagonists; (m) Immunosuppressive agents selected from the group consisting of cyclosporine, azathioprine, and methotrexate; or (n) anti-gout agents selected from the group consisting of colchicines.

In another aspect, the present invention provides a novel therapeutic method for treating a disease and/or condition in a mammal where the activity of $A_{2A}$ adenosine receptors is implicated (e.g., an adenosine $A_{2A}$ receptor associated state, such as glaucoma or ocular hypertension) and agonism of these receptors is desired, comprising: administering to a mammal in need thereof a therapeutically effective amount of an $A_{2A}$ agonist of the present invention or a stereoisomer or pharmaceutically acceptable salt thereof.

In another aspect, the present invention provides a novel therapeutic method for treating an adenosine $A_{2A}$ receptor associated state in a subject, comprising: administering to the subject an effective amount of an $A_{2A}$ agonist of the present invention or a stereoisomer or pharmaceutically acceptable salt thereof.

In another aspect, the adenosine $A_{2A}$ receptor associated state is selected from an autoimmune stimulation (e.g., arthritis, Crohn's disease, and chronic obstructive pulmonary disease (COPD)), inflammation, allergic diseases, skin diseases, infectious diseases (e.g., sepsis, Shiga toxin, *Clostridium difficile*, and *Clostridium difficile* toxin A-induced condition), wasting diseases, organ transplantation, tissue or cell transplantation (e.g., lung, bone marrow (graft versus host disease), kidney, and heart), neuropathic pain, open wounds, adverse effects from drug therapy, a cardiovascular condition, ischemia-reperfusion injury, dialysis, gout, chemical trauma, thermal trauma, diabetic nephropathy, diabetic foot ulcers, sickle cell disease, laminitis, founder's disease, glaucoma, ocular hypertension, spinal injury, myocardial infarction, acute myocardial infarction.

In another aspect, the adenosine $A_{2A}$ receptor associated state is selected from: arthritis, Crohn's disease, chronic obstructive pulmonary disease, sepsis, inflammatory bowel disease, glaucoma, ocular hypertension, diabetic nephropathy, tissue or cell transplantation, In another aspect, the adenosine $A_{2A}$ receptor associated state is arthritis.

In another aspect, the adenosine $A_{2A}$ receptor associated state is Crohn's disease.

In another aspect, the adenosine $A_{2A}$ receptor associated state is chronic obstructive pulmonary disease.

In another aspect, the adenosine $A_{2A}$ receptor associated state is sepsis.

In another aspect, the adenosine $A_{2A}$ receptor associated state is inflammatory bowel disease.

In another aspect, the adenosine $A_{2A}$ receptor associated state is glaucoma or ocular hypertension.

In another aspect, the adenosine $A_{2A}$ receptor associated state is diabetic nephropathy.

In another aspect, the adenosine $A_{2A}$ receptor associated state is tissue or cell transplantation.

In another aspect, the present invention provides the method of treating an inflammatory disorder, tissue activity or condition, comprising: administering an $A_{2A}$ agonist of the present invention or a stereoisomer or pharmaceutically acceptable salt thereof in combination with at least one other anti-inflammatory compound (e.g., a Type IV PDE inhibitor).

The inflammatory tissue activity, disorder or condition can be due to (a) pathological agents, (b) physical, chemical, or thermal trauma, or (c) the trauma of medical procedures, such as organ, tissue, or cell transplantation; angioplasty (PCTA); inflammation following ischemia/reperfusion; or, grafting. In yet another embodiment, the inflammatory disorder includes allergen-induced inflammation, ischemia-reperfusion injury, sepsis and autoimmune diseases. Without being bound by theory, stressed or injured tissues release endogenous adenosine, which blocks potentially destructive inflammatory cascades by binding to $A_{2A}$ adenosine receptors and decreasing activation of platelets, leukocytes and endothelial cells. In these tissues, adenosine acts by reducing expression of adhesion molecules and release of pro-inflammatory mediators (e.g., reactive oxygen species, elastase and tumor necrosis factor-alpha).

Further examples of inflammatory tissue activity or inflammatory disorders include inflammation due to: (a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers; Crohn's disease, ulcerative colitis, inflammatory bowel disease, osteoporosis and rheumatoid arthritis, chronic obstructive pulmonary disease (COPD); (b) allergic diseases such as asthma, hay fever, rhinitis, poison ivy, vernal conjunctivitis and other eosinophil-mediated conditions; (c) skin diseases such as psoriasis, contact dermatitis, eczema, infectious skin ulcers, healing of open wounds, cellulitis; (d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), lyme disease, HIV infection, (TNFα-enhanced HIV replication, TNFα inhibition of reverse transcriptase inhibitor activity), Shiga toxin, *Clostridium difficile*, and *Clostridium difficile* toxin A-induced condition; (e) wasting diseases: cachexia secondary to cancer and HIV; (f) organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, (e.g., interleukin-2 treatment), adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal trauma due to burns, acid, alkali and the like.

Additional diseases include, for example, equine disorders such as laminitis and founder's disease.

In another aspect, the present invention provides a method for treating neuropathic pain, comprising: intrathecally administering to a patient in need thereof a therapeutically effective amount of an $A_{2A}$ agonist of the present invention or a stereoisomer or a pharmaceutically acceptable salt thereof.

In another aspect, the present invention provides a method for treating biological diseases, comprising: administering a therapeutically effective amount of an anti-pathogenic agent (e.g., an antibiotic, antifungal, or antiviral agent) in combination with an $A_{2A}$ agonist of the present invention or a stereoisomer or a pharmaceutically acceptable salt thereof. If no anti-pathogenic agent is known, the $A_{2A}$ agonist can be used alone to reduce inflammation, as may occur during infection with antibiotic resistant bacteria or certain viruses (e.g., those that cause SARS, influenza, or Ebola). Optionally, the method further comprises administration of a type IV PDE inhibitor. The adenosine $A_{2A}$ receptor agonist can provide adjunctive therapy for treatment conditions such as the inflammation caused by sepsis, for example, human uremic syndrome when administered with antibiotics in the treatment of bio-terrorism weapons, such as anthrax, tularemia, *Escherichia coli*, Lyme disease, and plague. The adenosine $A_{2A}$ receptor agonists (e.g., a compound of formula 1a, 1b, 1 or of Table 1) can also provide adjunctive therapy for treatment of lethal pathogenic infections (e.g., bacterial, fungal, or viral)(e.g., anthrax, tularemia, *Escherichia coli*, and plague), comprising: administering an anti-pathogenic agent in combination with a compound of the present invention. Also included are yeast and fungal infections with or without anti-yeast or anti-fungal agents.

In another aspect, the invention provides a method to diagnose myocardial perfusion abnormalities in a subject comprising: (a) parenterally administering to said subject an $A_{2A}$ agonist of the present invention or a stereoisomer or a pharmaceutically acceptable salt thereof; and (b) performing a technique on said subject to detect the presence of coronary artery stenoses, assess the severity of coronary artery stenoses or both.

The compounds of the present invention can be used as a pharmacologic vasodilator agent that can be used with clinical perfusion imaging techniques, for example, for diagnosing and assessing the extent of coronary artery disease. Imaging techniques include planar or single photon emission computed tomography (SPECT), gamma camera scintigraphy, positron emission tomography (PET), nuclear magnetic resonance (NMR) imaging, magnetic resonance imaging (MRI), perfusion contrast echocardiography, digital subtraction angiography (DSA), and ultrafast X-ray computed tomography (CINE CT).

The compounds and compositions of the present invention can be administered as pharmacological stressors and used in conjunction with any one of several noninvasive diagnostic procedures to measure aspects of myocardial, coronary, and/or ventricular perfusion. Thus, the present invention provides a method for perfusion imaging in a subject, such as a human, comprising (1) administering an amount of an $A_{2A}$ agonist of the present invention or a stereoisomer or a pharmaceutically acceptable salt thereof to the subject, and (2) performing a technique on said subject to detect and/or determine the presence of an abnormality. Aspects that can be measured include coronary artery stenoses, myocardial dysfunction (e.g., myocardial ischemia, coronary artery disease, ventricular dysfunction, and differences in blood flow through disease-free coronary vessels and/or stenotic coronary vessels), myocardial contractile dysfunction, the presence of regional wall motion abnormalities, the functional significance of stenotic coronary vessels, coronary artery disease, ischemic ventricular dysfunction, and vasodilatory capacity (reserve capacity) of coronary arteries in humans. Radiopharmaceuticals are typically used in diagnostic methods. The radiopharmaceutical agent may comprise, for example, a radionuclide selected from the group consisting of thallium-201, technetium-99m, nitrogen-13, rubidium-82, iodine-123 and oxygen-15.

The compounds and compositions of the present invention can be administered as pharmacological stressors to assist with measuring fractional flow reserve (FFR), which is a technique used in coronary catheterization to measure pressure differences across a coronary artery stenosis.

The diagnostic methods of the present invention typically involve the administration of one or more $A_{2A}$ agonist of the present invention or a stereoisomer or a pharmaceutically acceptable salt thereof by intravenous infusion in doses which are effective to provide coronary artery dilation (approximately 0.25-500 mcg/kg/min, or 1-250 mcg/kg/min). However, its use in the invasive setting may involve the intracoronary administration of the drug in bolus doses of 0.1-50 mcg.

In another aspect, the adenosine $A_{2A}$ receptor agonist of the present invention is administered in combination with a therapeutic agent or procedure that treats glaucoma or ocular hypertension. Examples of such agents include alpha agonists (e.g., apraclonidineHCl, brimonidine tartrate), carbonic anhydrase inhibitors (e.g., brinzolamide, dorzolamideHCl, acetazolamide), prostaglandin analogs (e.g., travaprost, bimatoprost, latanoprost), beta blockers (e.g., timolol, betaxolol, levobunolol, metipranolol) and cholinergics (e.g., polocarpineHCl or carbachol). Examples of procedures that treat glaucoma or ocular hypertension include laser surgery, filtering microsurgery, glaucoma implants (e.g., shunts) or laser iridotomy.

In another aspect, the present invention provides a compound for use in therapy.

In another aspect, the present invention provides the use of compounds for the manufacture of a medicament for the treatment of an indication recited herein.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

"Adenosine $A_{2A}$ receptor agonist" includes compounds that activate the adenosine $A_{2A}$ receptor with a $K_i$ of <1 μM as determined by a known binding assay. An adenosine $A_{2A}$ receptor agonist may also be cross reactive with other adenosine receptor subtypes (e.g., $A_1$, $A_{2B}$, and $A_3$). In one embodiment, the adenosine $A_{2A}$ receptor agonist may be selective for $A_{2A}$ (e.g., at least 2, 10, 50, or 100/1 over another adenosine receptor subtype) or may activate/antagonize other receptors with a greater or lesser affinity than the $A_{2A}$ receptor. In other embodiments, the adenosine $A_{2A}$ receptor agonist is a compound of formula Ia, Ib, 1 or of Table 1.

"Adenosine $A_{2A}$ receptor associated state" includes those diseases or disorders which are directly or indirectly implicated in the adenosine $A_{2A}$ receptor pathway. Without being bound by theory, it is thought that administration of an adenosine $A_{2A}$ agonist upregulates the biological activity of the adenosine $A_{2A}$ receptor by the binding of the agonist to the receptor, thereby activating the receptor and triggering the downstream biological pathway associated with the activity of the adenosine $A_{2A}$ receptor. Accordingly, an adenosine $A_{2A}$ receptor associated state includes those diseases and disorders directly associated with the inactivity or downregulation of the adenosine $A_{2A}$ receptor or the inactivity or downregulation of the biological pathway associated with the adenosine $A_{2A}$ receptor. Examples of adenosine $A_{2A}$ receptor associated states include inflammatory disorders and tissue activity, sickle cell disease, sepsis, septic shock, meningitis, peritonitis, arthritis, hemolytic uremic syndrome, glaucoma and ocular hypertension.

"Reducing ocular hypertension" includes the decrease and/or the complete elimination of ocular hypertension. In one embodiment, the intraocular pressure is reduced by about 5%, 10%, 15%, 20%, 25%, 30%, 35%, 40%, 45%, 50%, 55%, 60%, 65%, 70%, 75%, 80%, 85%, 90%, 95% to 100% compared to the intraocular pressure prior to treatment.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Glaucoma" includes a group of eye conditions that lead to damage to the optic nerve, the nerve that carries visual information from the eye to the brain. It is an intractable eye disease which exhibits increased intraocular pressure due to a variety of factors and involves a risk of leading to blindness. It is known that the incidence rate of glaucoma increases with age, and the progression of optic nerve injury also accelerates with age. In many cases, damage to the optic nerve is due to increased pressure in the eye, also known as intraocular pressure (IOP). Glaucoma includes open-angle glaucoma, which includes symptoms such as a gradual loss or peripheral vision (also called tunnel vision); angle-closure glaucoma, which includes symptoms such as sudden, severe pain in one eye, decreased or cloudy vision, nausea and vomiting, rainbow-like halos around lights, red and/or swollen eye; and congenital glaucoma, which includes symptoms that are usually noticed when the child is a few months old, such as cloudiness of the front of the eye, enlargement of one eye or both eyes, red eye and sensitivity to light.

"Ocular hypertension" refers to the condition in which the intraocular pressure is higher than normal, in the absence of optic nerve damage or visual field loss. One of skill in the art would understand that normal intraocular pressure is between about 10 mmHg and 20 mmHg, where the average value of intraocular pressure is 15.5 mmHg with fluctuations of about 2.75 mmHg. The language "intraocular pressure" refers to the fluid pressure of the aqueous humor inside the eye.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

Examples of the molecular weight of the compounds of the present invention include (a) less than about 500, 550, 600, 650, 700, 750, 800, 850, 900, 950, or 1000 grams per mole; (b) less than about 950 grams per mole; (c) less than about 850 grams per mole; and, (d) less than about 750 grams per mole.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

"Stable" means that the compound is suitable for pharmaceutical use.

The present invention covers stable compounds and thus avoids, unless otherwise specified, the following bond types: heteroatom-halogen, N—S, O—S, O—O, and S—S.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

When an "ene" terminates a group it indicates the group is attached to two other groups. For example, methylene refers to a —$CH_2$— moiety.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$alkenyl includes $C_2$, $C_3$, $C_4$, $C_5$, and $C_6$alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$Alkynyl includes $C_2$, $C_3$, $C_4$, $C_5$, and $C_6$alkynyl groups.

"Alkoxy" includes alkyl, alkenyl, and alkynyl groups covalently linked to an oxygen atom. Examples of alkoxy groups include methoxy, ethoxy, isopropyloxy, propoxy, t-butyloxy, isobutyloxy, butoxy, and pentoxy groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperidine.

"Halo" or "halogen" refers to fluoro, chloro, bromo, and iodo.

"Counterion" is used to represent a small, negatively charged species, such as chloride, bromide, hydroxide, acetate, and sulfate.

The group "$C_6H_4$" represents a phenylene.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "heterocycle" or "heterocyclyl" includes stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbon atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

Examples of heterocycles include, but are not limited to, decahydroquinolinyl, imidazolidinyl, imidazolinyl, indolinyl, isatinoyl, methylenedioxyphenyl, morpholinyl, octahydroisoquinolinyl, oxazolidinyl, oxindolyl, piperazinyl, piperidinyl, piperidonyl, 4-piperidonyl, piperonyl, pyranyl, pyrazolidinyl, pyrazolinyl, pyrrolidinyl, pyrrolinyl, tetrahydrofuranyl, tetrahydroisoquinolinyl, tetrahydroquinolinyl, 1-aza-bicyclo[2.2.2]octane, 2,5-diaza-bicyclo[2.2.2]octane, and 2,5-diaza-bicyclo[2.2.1]heptane. Also included are fused ring and spiro compounds containing, for example, the above heterocycles.

"Mammal" and "patient" cover warm blooded mammals that are typically under medical care (e.g., humans and domesticated animals). Examples include feline, canine, equine, bovine, non-human primate, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting its development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to an indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Formulations and Dosages

The adenosine $A_{2A}$ receptor agonists of the present invention can be formulated as pharmaceutical compositions and administered to a mammalian host, such as a human patient in a variety of forms adapted to the chosen route of administration, e.g., orally or parenterally, by intravenous (e.g., continuously or bolus), intrathecal, intramuscular, topical, intradermal, intraperitoneal, intraocular, inhalation or subcutaneous routes. Exemplary pharmaceutical compositions are disclosed in "Remington: The Science and Practice of Pharmacy," A. Gennaro, ed., 20th edition, Lippincott, Williams & Wilkins, Philadelphia, Pa.

Thus, the present compounds may be systemically administered, e.g., orally, in combination with a pharmaceutically acceptable carrier/excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The amount of the adenosine $A_{2A}$ receptor agonist of the present invention or an active salt or derivative thereof, required for use in treatment will vary not only with the particular compound or salt selected but also with the route of administration, the nature of the condition being treated, and the age and condition of the patient, and will ultimately be at the discretion of the attendant physician or clinician. In general, however, a suitable dose will be in the range of (a) about 1.0-100 mg/kg of body weight per day, (b) about 10-75 mg/kg of body weight per day, and (c) about 5-20 mg/kg of body weight per day.

For an eye drop, the composition will typically contain an active ingredient at a concentration of generally from 0.000001 to 10% (w/v), also from 0.00001 to 3% (w/v), 0.0001 to 1% (w/v), and 0.001 to 0.1% (w/v) may be instilled to an adult once to several times a day.

For oral administration, the adenosine $A_{2A}$ receptor agonists of the present invention may be administered to an adult once or divided into several times at a dose of generally from 0.001 to 5000 mg per day, also from 0.1 to 2500 mg per day, and from 1 to 1000 mg per day.

For a liquid composition (e.g., in a lotion), the concentration of adenosine $A_{2A}$ receptor agonists of the present invention can be from (a) about 0.1-25 wt % and (b) about 0.5-10 wt %. The concentration in a semi-solid or solid composition such as a gel or a powder can be (a) about 0.1-5 wt % and (b) about 0.5-2.5 wt %.

The adenosine $A_{2A}$ receptor agonists of the present invention can be conveniently administered in unit dosage form; e.g., tablets, caplets, etc., containing (a) about 4-400 mg, (b) about 10-200 mg, and (c) about 20-100 mg of active ingredient per unit dosage form.

The adenosine $A_{2A}$ receptor agonists of the present invention can be administered to achieve peak plasma concentrations of the active compound of (a) about 0.02-μM, (b) about 0.1-10 μM, and (c) about 0.5-5 μM. These concentrations may be achieved, for example, by the intravenous injection (e.g., continuously or bolus) of a 0.005-0.5% solution of the active ingredient, or orally administered as a bolus containing about 4-400 mg of the active ingredient.

When an adenosine $A_{2A}$ receptor agonist of the present invention is administered in combination with another agent or agents (e.g., co-administered), then the adenosine $A_{2A}$ receptor agonist of the present invention and other agent can be administered simultaneously or in any order. They can be administered as a single pharmaceutical composition or as separate compositions. The administration of the adenosine $A_{2A}$ receptor agonist of the present invention can be prior to the other agent(s), within minutes thereof, or up to hours (e.g., 24 or 48) or even days after the administration of the other agent(s). For example, the administration of the adenosine $A_{2A}$ receptor agonist of the present invention can be within about 24 hours or within about 12 hours.

The preventive or therapeutic adenosine $A_{2A}$ receptor agonists of the present invention for treating glaucoma or ocular hypertension can be administered, e.g., either orally or parenterally. Examples of the dosage form include eye drops, ophthalmic ointments, injections, tablets, capsules, granules, powders and the like. In particular, eye drops are preferred. These can be prepared using any of generally used techniques. For example, in the case of eye drops, a desired eye drop can be prepared by adding the present compound to purified water or a buffer or the like, stifling the mixture, and then adjusting the pH of the solution with a pH adjusting agent. Further, an additive which is generally used in eye drops can be used as needed. For example, preparation thereof can be carried out using a tonicity agent such as sodium chloride or concentrated glycerin, a buffer such as sodium phosphate, sodium acetate, boric acid, borax or citric acid, a surfactant such as polyoxyethylenesorbitanmonooleate, polyoxyl stearate or polyoxyethylene hydrogenated castor oil, a stabilizer such as sodium citrate or sodium ethylenediaminetetraacetate (EDTA), a preservative such as benzalkonium chloride or paraben, and the like. The pH of the eye drops is permitted as long as it falls within the range that is acceptable as an ophthalmic preparation, but is preferably in the range of from 3 to 8. The ophthalmic ointments can be prepared with a generally used base such as white petrolatum or liquid paraffin. Also, oral preparations such as tablets, capsules, granules and powders can be prepared by adding an extender such as lactose, crystalline cellulose, starch or vegetable oil, a lubricant such as magnesium stearate or talc, a binder such as hydroxypropyl cellulose or polyvinyl pyrrolidone, a disintegrant such as carboxymethyl cellulose calcium or low-substituted hydroxypropylmethyl cellulose, a coating agent such as hydroxypropylmethyl cellulose, macrogol or a silicone resin, a film forming agent such as gelatin film, and the like, as needed.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The adenosine $A_{2A}$ receptor agonists of the present invention may also be administered intravenously (e.g., continuously or bolus) or intraperitoneally by infusion or injection. Solutions of the adenosine $A_{2A}$ receptor agonists of the present invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the adenosine $A_{2A}$ receptor agonists of the present invention may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Examples of useful dermatological compositions which can be used to deliver the adenosine $A_{2A}$ receptor agonists of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The adenosine $A_{2A}$ receptor agonists of the present invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, and atomizers are fully described in pharmaceutical reference books such as *Remington's Pharmaceutical Sciences* Volumes 16 (1980) or 18 (1990) Mack Publishing Co.

The desired dose of the adenosine $A_{2A}$ receptor agonists of the present invention may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Synthesis

The compounds of the present invention can be prepared in a number of ways known to one skilled in the art of organic synthesis (e.g., see U.S. Pat. No. 6,476,060 B2, and *J Med Chem* 2004, 47, 627). The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

One stereoisomer of a compound of the present invention may be a more potent $A_{2A}$ agonist than its counterpart(s). Thus, stereoisomers are included in the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Other features of the invention will become apparent in the course of the following descriptions of exemplary embodiments that are given for illustration of the invention and are not intended to be limiting thereof.

EXAMPLES

The following examples are representative of the procedures used to prepare the compounds of the present invention.

General Procedure for the Synthesis of N-alkynyl-nicotinamides

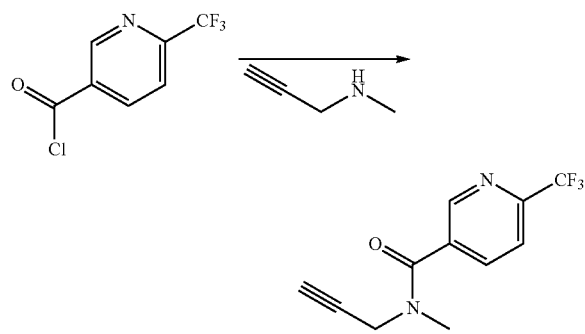

N-methyl-N-(prop-2-ynyl)-6-(trifluoromethyl)nicotinamide

N-methylpropargylamine (95%, 1.0 g, 13.75 mmol) and pyridine (5 mL) in dry dichloromethane (DCM)(50 mL) were cooled with ice-water. 6-(Trifluoromethyl)pyridine-3-carbonyl chloride (97%, 2.83 g, 13.10 mmol) was added drop wise with a syringe. The ice bath was removed and the mixture was stirred at room temperature overnight. DCM (150 mL) was added and the mixture was washed with water (3×100 mL). The organic phase was dried with anhydrous MgSO₄, filtered and evaporated to dryness, then purified by silica gel column chromatography, eluting with MeOH/DCM (0-2%) to give the product (1.96 g, 70.0% yield), LRMS ESI (M+H+) 243, HPLC rt=5.4 min.

General Procedure for the Synthesis of N-alkynyl-benzamides

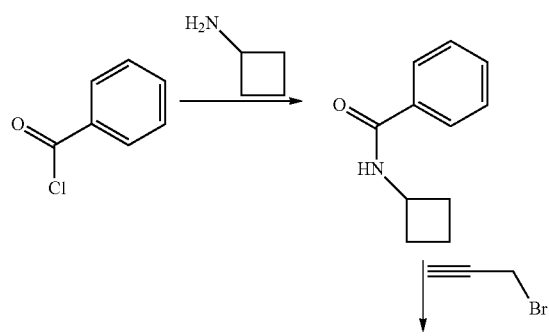

-continued

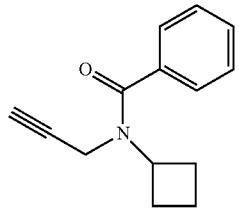

N-cyclobutyl-N-(prop-2-ynyl)benzamide

A mixture of benzoyl chloride (10.90 mL, 94.60 mmol) in ether (250 mL) and water (150 mL) was cooled over ice. Potassium carbonate (14.62 g, 105.78 mmol) was added followed by drop wise addition of cyclobutylamine (6.00 mL, 70.28 mmol). The ice was removed and the mixture stirred at 25° C. for 48 hours. DCM (350 mL) was added and the mixture washed with water (2×250 mL). The aqueous was back extracted with DCM (2×150 mL). The combined organic extracts were dried over MgSO₄, filtered and evaporated to dryness under reduced vacuum to afford the crude N-(cyclobutyl)benzamide (12.14 g, 69.26 mmol, 98.6% yield) which was used directly in the next reaction.

A solution of the N-(cyclobutyl)benzamide (12.14 g, 69.2621 mmol) in THF (225 mL) was cooled to 5° C. over ice. A solution of n-butyl lithium (1.6 M in hexanes, 54.00 mL, 86.40 mmol) was added drop wise and the mixture stirred over ice for 15 minutes. A solution of propargyl bromide in toluene (80% wt., 10.30 mL, 92.47 mmol) was added drop wise. The ice was removed and the mixture stirred for 46 hours. Approximately half of the THF was evaporated under reduced vacuum. The mixture was poured over ice water (125 mL) and extracted with DCM (3×125 mL). The combined organic layers were washed with brine (125 mL), dried over MgSO₄, filtered and evaporated to dryness to afford the crude N-cyclobutyl-N-(prop-2-yn-1-yl)benzamide (16.33 g, 76.54 mmol). The crude material was divided into three equal portions, each of which was purified by column chromatography (Si=170 g), eluting with EtOAc/hexanes (0-8%). Like fractions were collected and combined to afford the purified N-cyclobutyl-N-(prop-2-yn-1-yl)benzamide (10.86 g, 50.90 mmol, 73.5%), LRMS ESI (M+H+) 214.

General Procedure for the Synthesis of N-alkynyl-acetamides

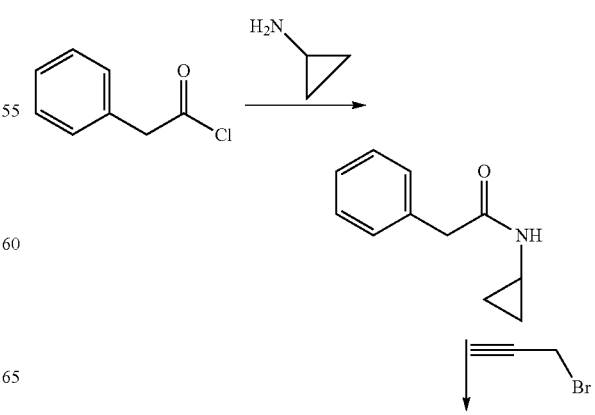

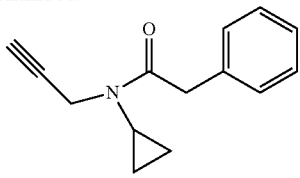

N-cyclopropyl-2-phenyl-N-(prop-2-ynyl)acetamide

Cyclopropylamine (98%, 1.0 g, 17.17 mmol) and pyridine (5 mL) in dry DCM (50 mL) were cooled with ice-water. 2-Phenylacetyl chloride (98%, 2.58 g, 16.36 mmol) was added dropwise with a syringe. The ice bath was removed and the mixture was stirred at room temperature overnight. DCM (150 mL) was added and the mixture was washed with water (3×100 mL). The organic phase was dried with anhydrous MgSO₄, filtered and evaporated to dryness, then used in the next step.

Sodium hydride (60% in mineral oil, 706 mg, 17.65 mmol) was washed with dry ether (2×20 mL) and then suspended in dry THF (30 mL) and cooled with ice-water. Crude N-cyclopropyl-2-phenylacetamide from the last step in THF (5 mL) was added dropwise at 5° C. to the sodium hydride suspension. The reaction mixture was stirred at 5° C. for 20 min. A solution of propargyl bromide in toluene (80% wt., 2.68 mL, 24.06 mmol) was added dropwise with a syringe. The ice bath was removed and the mixture was stirred at room temperature overnight. The mixture was poured into ice-water (100 mL) and extracted with DCM (3×100 mL). The organic phases were combined and washed with brine (2×50 mL), dried with anhydrous MgSO₄, filtered and evaporated to dryness, then purified by silica gel column chromatography, eluting with MeOH/DCM (0-2%) to give the title compound (2.05 g, 58.8% yield), LRMS ESI (M+H⁺) 214.

General Procedure for the Synthesis of N-benzyl-N-alkynyl-carboxamides

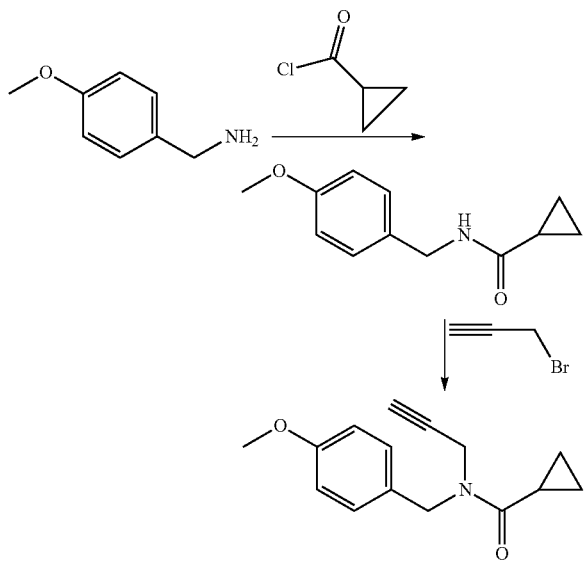

N-(4-Methoxybenzyl)-N-(prop-2-ynyl)cyclopropanecarboxamide

4-Methoxybenzylamine (98%, 4.0 g, 16.11 mmol) and pyridine (5 mL) in dry DCM (50 mL) were cooled with ice-water. Cyclopropanecarbonyl chloride (98%, 1.57 mL, 16.96 mmol) was added dropwise with a syringe. The ice bath was removed and the mixture was stirred at room temperature overnight. DCM (150 mL) was added and the mixture was washed with water (3×100 mL). The organic phase was dried with anhydrous MgSO₄, filtered and evaporated to dryness, then used in the next step.

Sodium hydride (60% in mineral oil, 709 mg, 17.72 mmol) was washed with dry ether (2×20 mL) and then suspended in dry THF (30 mL) and cooled with ice-water. Crude N-(4-methoxybenzyl)cyclopropanecarboxamide from last step in THF (5 mL) was added dropwise at 5° C. to the sodium hydride suspension. The reaction mixture was stirred at 5° C. for 20 min. A solution of propargyl bromide in toluene (80% wt., 2.69 mL, 24.17 mmol) was added dropwise with a syringe. The ice bath was removed and the mixture was stirred at room temperature overnight. The mixture was poured into ice-water (100 mL) and extracted with DCM (3×100 mL). The organic phases were combined and washed with brine (2×50mL), dried with anhydrous MgSO₄, filtered and evaporated to dryness, then purified by silica gel column chromatography, eluting with MeOH/DCM (0-2%) to give the product (2.43 g, 62.0% yield), LRMS ESI (M+H⁺) 244.

General Procedure for the Synthesis of 2-alkynyl adenosine-5'-uronamides

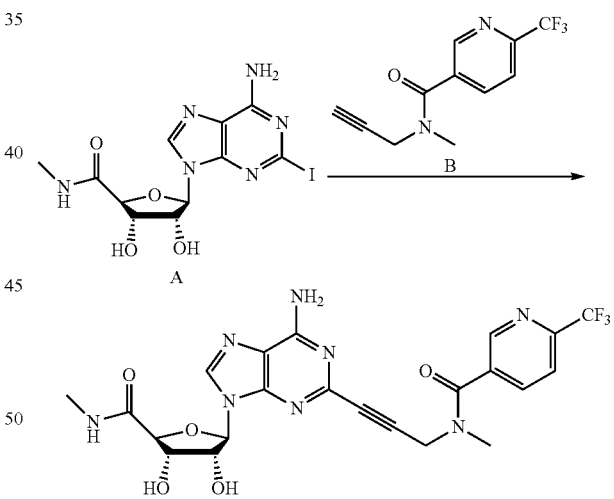

To a solution of N-methyl 2-iodoadenosine-5'-uronamide (0.45 mmol)(structure A above) in freshly degassed THF (35 mL) was added potassium carbonate (1.9 mmol), copper(I) iodide (0.21 mmol), palladium (0) tetrakistriphenylphosphine (0.057 mmol) and the corresponding alkyne (0.85 mmol)(e.g., for Example 1, N-methyl-N-(prop-2-yn-1-yl)-6-(trifluoromethyl)nicotinamide, structure B above). The mixture was stirred at room temperature under an inert atmosphere for 20 to 24 h. Silica bound Pd(II) scavenger Si-Thiol (225 mg) and Pd(0) scavenger Si-TAAcOH (475 mg) were added and stirring continued a further 24 h. The suspension was filtered and the resulting solution evaporated to dryness. The crude was purified by chromatography on a 43 g column (2.1 cm×30 cm) of 40-60 μM silica gel eluting with a gradient of DCM/MeOH to afford the pure product.

Example 1

N-Methyl 2-(3-{N-methyl-1-[6-(trifluoromethyl)pyridin-3-yl]formamido}prop-1-yn-1-yl)adenosine-5'-uronamide Using the general procedure for the synthesis of 2-alkynyl adenosine-5'-uronamides above, N-methyl 2-iodoadenosine-5'-uronamide (98 mg) and N-methyl-N-(prop-2-yn-1-yl)-6-(trifluoromethyl)nicotinamide gave the title compound as an off-white solid: yield 29 mg, 23%. LRMS ESI (M+H$^+$) 535.35. HPLC rt=4.3 min.

Example 2

N-Cyclopropyl 2-(3-{N-methyl-1-[6-(trifluoromethyl)pyridin-3-yl]formamido}prop-1-yn-1-yl)adenosine-5'-uronamide Using the general procedure for the synthesis of 2-alkynyl adenosine-5'-uronamides above, N-cyclopropyl 2-iodoadenosine-5'-uronamide (98 mg) and N-methyl-N-(prop-2-yn-1-yl)-6-(trifluoromethyl)nicotinamide gave the title compound as an off-white solid: yield 52 mg, 42%. LRMS ESI (M+H$^+$) 561.40. HPLC rt=4.8 min.

Example 3

N-Cyclopropyl 2-{3-[N-(cyclopropylmethyl)benzamido]propyn-1-yl}adenosine-5'-uronamide Using the general procedure for the synthesis of 2-alkynyl adenosine-5'-uronamides above, N-cyclopropyl 2-iodoadenosine-5'-uronamide (63 mg) and N-(cyclopropylmethyl)-N-(prop-2-yn-1-yl)benzamide gave the title compound as a brown solid: yield 32 mg, 42%. LRMS ESI (M+H$^+$) 532.40. HPLC rt=6.7 min.

Example 4

N-Cyclopropyl 2-{3-[N-(cyclobutyl)benzamido]propyn-1-yl}adenosine-5'-uronamide

Using the general procedure for the synthesis of 2-alkynyl adenosine-5'-uronamides above, N-cyclopropyl 2-iodoadenosine-5'-uronamide (73 mg) and N-cyclobutyl-N-(prop-2-yn-1-yl)benzamide gave the title compound as a brown solid: yield 35 mg, 40%. LRMS ESI (M+H$^+$) 532.40. HPLC rt=6.9 min.

Example 5

N-Cyclopropyl 2-{3-[benzamido]propyn-1-yl}adenosine-5'-uronamide

Using the general procedure for the synthesis of 2-alkynyl adenosine-5'-uronamides above, N-cyclopropyl 2-iodoadenosine-5'-uronamide (58 mg) and N-(prop-2-yn-1-yl)benzamide gave the title compound as a brown solid: yield 21 mg, 45%. LRMS ESI (M+H$^+$) 478.30. HPLC rt=4.2 min.

Example 6

N-Methyl 2-{3-[N-methyl-1-(6-fluoropyridin-3-yl)formamido]prop-1-yn-1-yl}adenosine-5'-uronamide Using the general procedure for the synthesis of 2-alkynyl adenosine-5'-uronamides above, N-methyl 2-iodoadenosine-5'-uronamide (97 mg) and 6-fluoro-N-methyl-N-(prop-2-yn-1-yl)nicotinamide gave the title compound as an off-white solid: yield 15 mg, 13%. LRMS ESI (M+H$^+$) 485.35. HPLC rt=2.8 min.

Example 7

N-Cyclopropyl 2-{3-[N-methyl-1-(6-fluoropyridin-3-yl)formamido]prop-1-yn-1-yl}adenosine-5'-uronamide Using the general procedure for the synthesis of 2-alkynyl adenosine-5'-uronamides above, N-cyclopropyl 2-iodoadenosine-5'-uronamide (97 mg) and 6-fluoro-N-methyl-N-(prop-2-yn-1-yl)nicotinamide gave the title compound as an off-white solid: yield 30 mg, 27%. LRMS ESI (M+H$^+$) 511.40. HPLC rt=3.2 min.

Example 8

N-Methyl 2-{3-[N-(cyclobutyl)benzamido]propyn-1-yl}adenosine-5'-uronamide

Using the general procedure for the synthesis of 2-alkynyl adenosine-5'-uronamides above, N-methyl 2-iodoadenosine-5'-uronamide (191 mg) and N-cyclobutyl-N-(prop-2-yn-1-yl)benzamide gave the title compound as a brown solid: yield 124 mg, 54%. LRMS ESI (M+H$^+$) 506.35. HPLC rt=6.6 min.

Example 9

N-Methyl 2-{3-[N-methylnicotinamido]propyn-1-yl}adenosine-5'-uronamide

Using the general procedure for the synthesis of 2-alkynyl adenosine-5'-uronamides above, N-methyl 2-iodoadenosine-5'-uronamide (100 mg) and N-methyl-N-(prop-2-yn-1-yl)nicotinamide gave the title compound as a brown solid: yield 28 mg, 25%. LRMS ESI (M+H$^+$) 467.30. HPLC rt=2.5 min.

Example 10

N-Methyl 2-{3-[N-methylisonicotinamido]propyn-1-yl}adenosine-5'-uronamide

Using the general procedure for the synthesis of 2-alkynyl adenosine-5'-uronamides above, N-methyl 2-iodoadenosine-5'-uronamide (94 mg) and N-methyl-N-(prop-2-yn-1-yl)isonicotinamide gave the title compound as a brown solid: yield 26 mg, 25%. LRMS ESI (M+H$^+$) 467.30. HPLC rt=2.3 min.

Example 11

N-Methyl 2-{3-[6-fluoro-N-(2-methoxyethyl)nicotinamido]propyn-1-yl}adenosine-5'-uronamide Using the general procedure for the synthesis of 2-alkynyl adenosine-5'-uronamides above, N-methyl 2-iodoadenosine- 5'-uronamide (80 mg) and 6-fluoro-N-(2-methoxyethyl)-N-(prop-2-yn-1-yl)nicotinamide gave the title compound as a brown solid: yield 50 mg, 50%. LRMS ESI (M+H$^+$) 529.35. HPLC rt=3.3 min.

Example 12

N-Methyl 2-{3-[N-(2-methoxyethyl)thiophene-2-carboxamido]propyn-1-yl}adenosine-5'-uronamide Using the general procedure for the synthesis of 2-alkynyl adenosine-5'-uronamides above, N-methyl 2-iodoadenosine-5'-uronamide (78 mg) and N-(2-methoxyethyl)-N-(prop-2-yn-1-yl)thiophene-2-carboxamide gave the title compound as a brown solid: yield 44 mg, 46%. LRMS ESI (M+H$^+$) 516.30. HPLC rt=4.4 min.

Example 13

N-Methyl 2-{3-[N-methylbenzamido]propyn-1-yl}adenosine-5'-uronamide

Using the general procedure for the synthesis of 2-alkynyl adenosine-5'-uronamides above, N-methyl 2-iodoadenosine-5'-uronamide (89 mg) and N-methyl-N-(prop-2-yn-1-yl)benzamide gave the title compound as a brown solid: yield 33 mg, 33%. LRMS ESI (M+H$^+$) 466.30. HPLC rt=4.1 min.

Example 14

N-Methyl 2-{3-[N-(2-methoxyethyl)benzamido]propyn-1-yl}adenosine-5'-uronamide

Using the general procedure for the synthesis of 2-alkynyl adenosine-5'-uronamides above, N-methyl 2-iodoadenosine-5'-uronamide (94 mg) and N-(2-methoxyethyl)-N-(prop-2-yn-1-yl)benzamide gave the title compound as a brown solid: yield 91 mg, 79%. LRMS ESI (M+H$^+$) 510.35. HPLC rt=4.7 min.

Example 15

N-Methyl 2-{3-[4-fluoro-N-methylbenzamido]propyn-1-yl}adenosine-5'-uronamide

Using the general procedure for the synthesis of 2-alkynyl adenosine-5'-uronamides above, N-methyl 2-iodoadenosine-5'-uronamide (99 mg) and 4-fluoro-N-methyl-N-(prop-2-yn-1-yl)benzamide gave the title compound as a brown solid: yield 59 mg, 52%. LRMS ESI (M+H$^+$) 484.30. HPLC rt=4.4 min.

Examples 16-36 in Table 1 are compounds of the present invention that were synthesized using the methods described above from the corresponding iodo-uronamide and 2-substituted-propyn-1-yl. The starting 2-substituted-propyn-1-yl groups were prepared according to the general procedures provided above.

In Table 1, M.S. is LRMS ESI (M+H$^+$). General HPLC Conditions for determining purity: Gradient of 40% methanol (0.1% Formic acid)/60% water (0.1% Formic acid) to 80% methanol (0.1% Formic acid)/20% water (0.1% Formic acid) over 15 minutes. UV at 270 nm. Retention times (RT) are shown below.

The binding of $A_{2A}$ Ki values for tested compounds is provided in Table 1. The Ki values were obtained using the methodology described by Murphree et al. in *Mol Pharmacol* 2002, 61, 455-62.

TABLE 1

| Ex # | Structure | LRMS ESI (M + H+) Ret. Time (RT) | Ki |
|---|---|---|---|
| 1. | 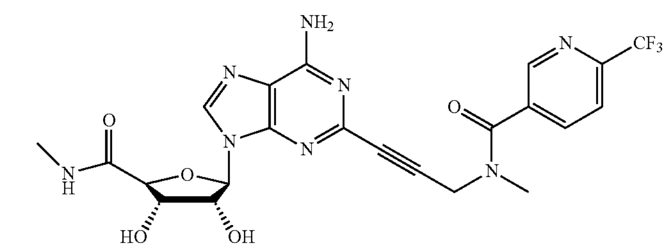 | 535.40 4.3 min | + |
| 2. | 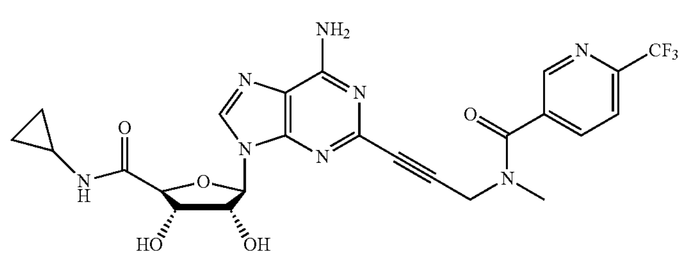 | 561.40 4.8 min | + |

TABLE 1-continued

| Ex # | Structure | LRMS ESI (M + H+) Ret. Time (RT) | Ki |
|---|---|---|---|
| 3. | 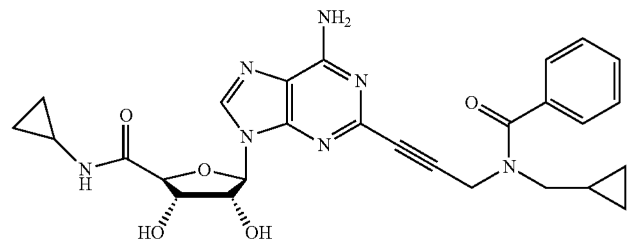 | 532.40<br>6.7 min | + |
| 4. | 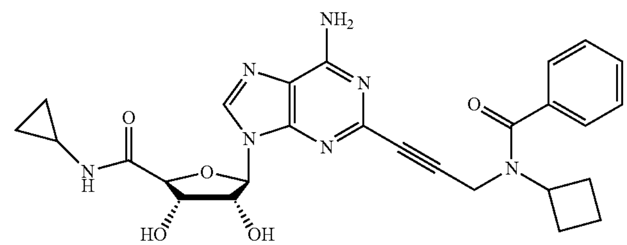 | 532.40<br>6.9 min | + |
| 5. | 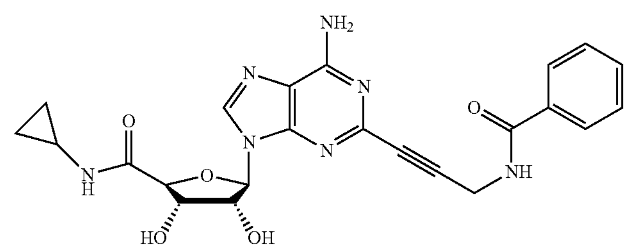 | 478.30<br>4.2 min | ++ |
| 6. | 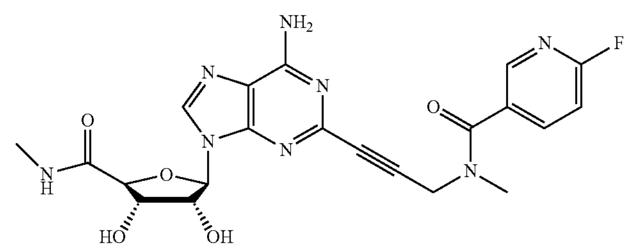 | 485.35<br>2.9 min | + |
| 7. | 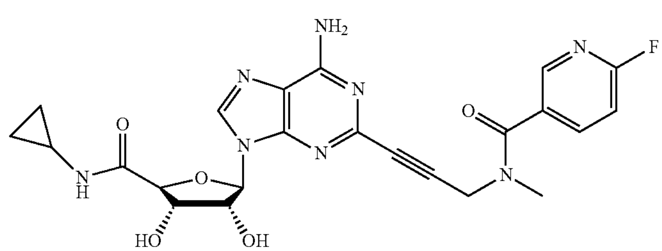 | 511.40<br>3.2 min | ++ |
| 8. | 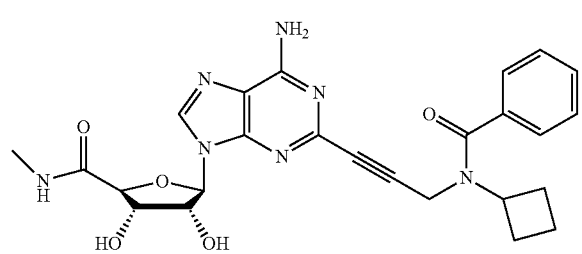 | 506.35<br>6.6 min | + |

TABLE 1-continued
| Ex # | Structure | LRMS ESI (M + H+) Ret. Time (RT) | Ki |
|---|---|---|---|
| 9. | 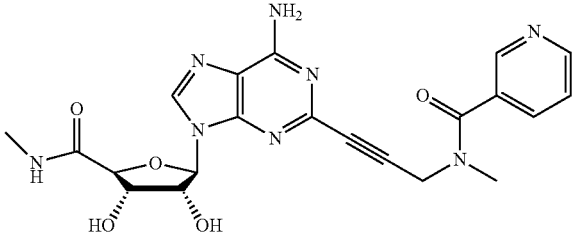 | 467.30 2.5 min | ++ |
| 10. | 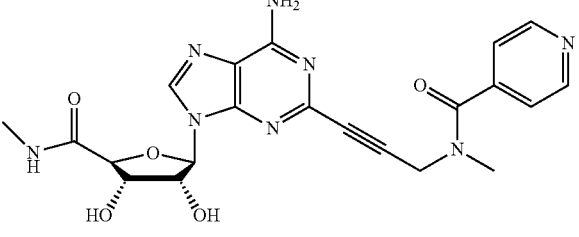 | 467.30 2.3 min | ++ |
| 11. | 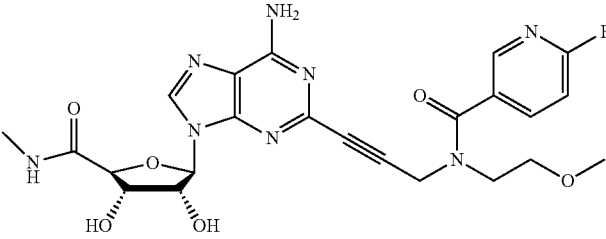 | 529.35 3.3 min | + |
| 12. | 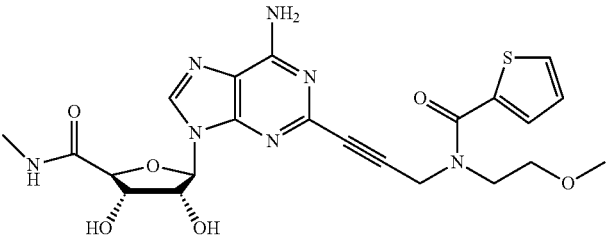 | 516.30 4.4 min | + |
| 13. | 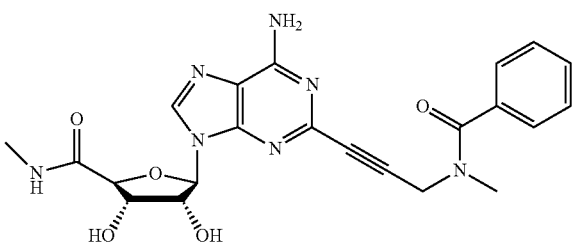 | 466.30 4.1 min | + |
| 14. | 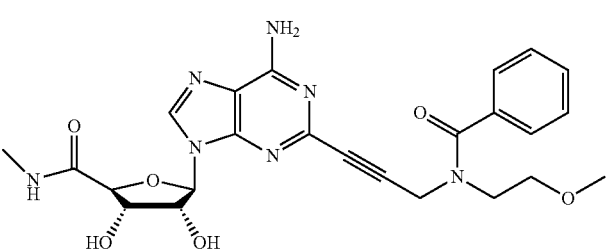 | 510.35 4.7 min | + |

TABLE 1-continued

| Ex # | Structure | LRMS ESI (M + H+) Ret. Time (RT) | Ki |
|---|---|---|---|
| 15. | 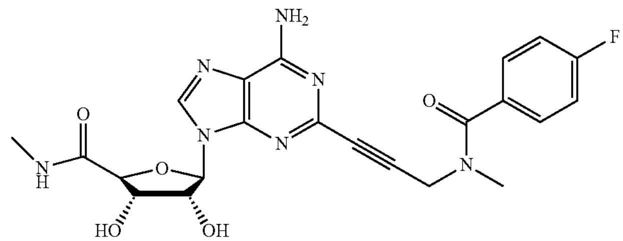 | 484.30 4.4 min | + |
| 16. | 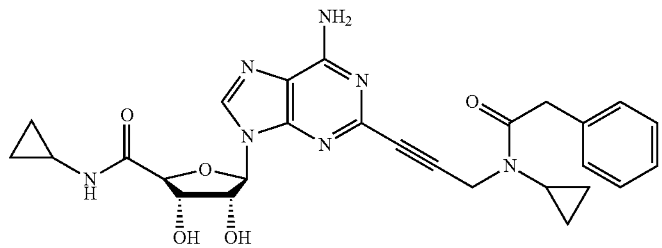 | 532.45 7.5 min | ++ |
| 17. | 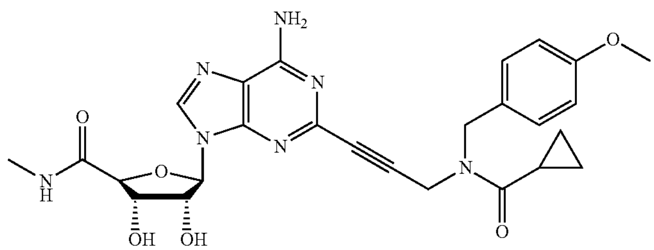 | 536.40 7.2 min | ++ |
| 18. | 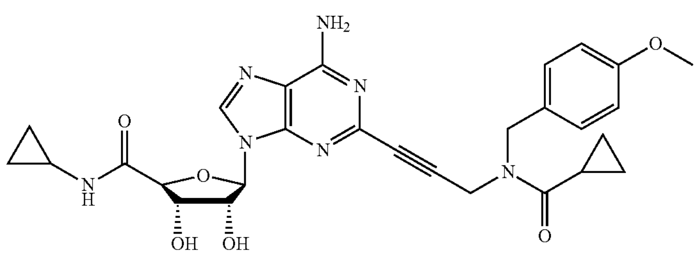 | 562.45 7.4 min | + |
| 19. | 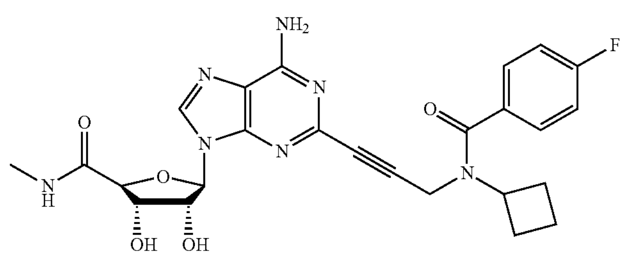 | 524.40 8.2 min | + |
| 20. | 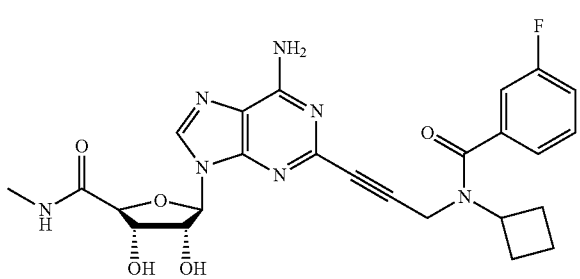 | 524.35 8.2 min | + |

TABLE 1-continued

| Ex # | Structure | LRMS ESI (M + H+) Ret. Time (RT) | Ki |
|---|---|---|---|
| 21. | 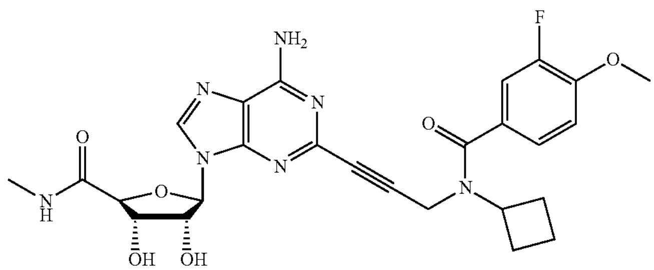 | 554.35 8.3 min | + |
| 22. | 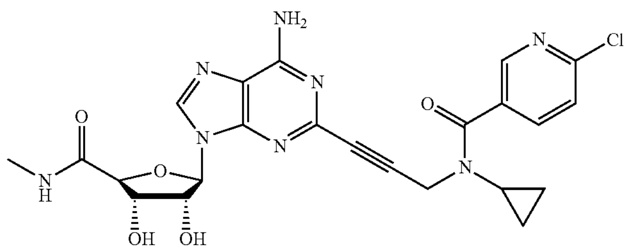 | 527.40 6.2 min | + |
| 23. | 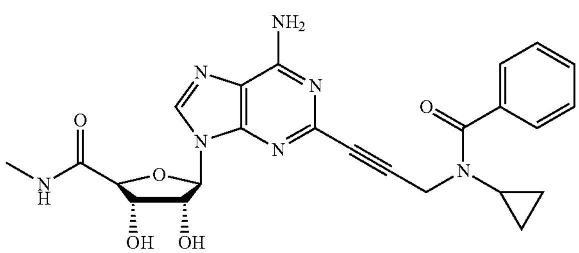 | 492.40 6.9 min | +++ |
| 24. | 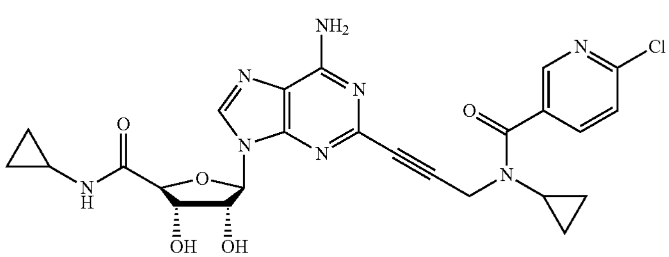 | 553.40 6.3 min | + |
| 25. | 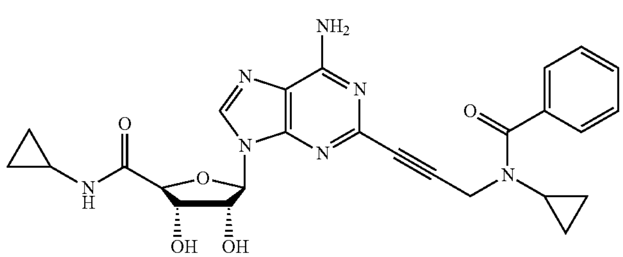 | 518.45 7.0 min | + |

TABLE 1-continued

| Ex # | Structure | LRMS ESI (M + H+) Ret. Time (RT) | Ki |
|---|---|---|---|
| 26. | 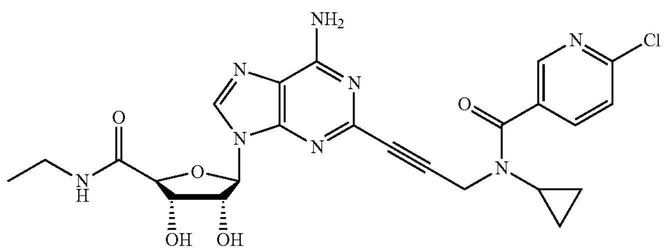 | 541.40 6.5 min | + |
| 27. | 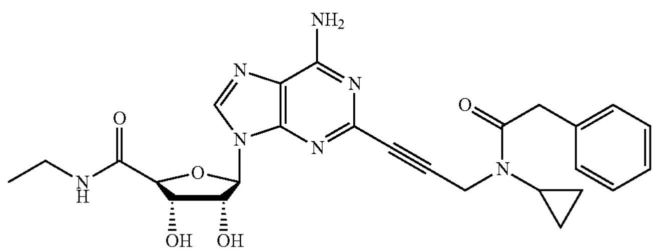 | 520.50 7.6 min | ++ |
| 28. | 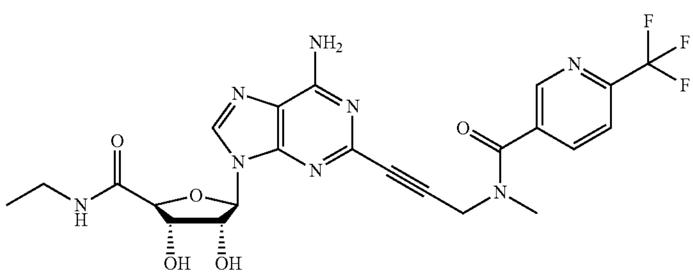 | 549.45 6.3 min | + |
| 29. | 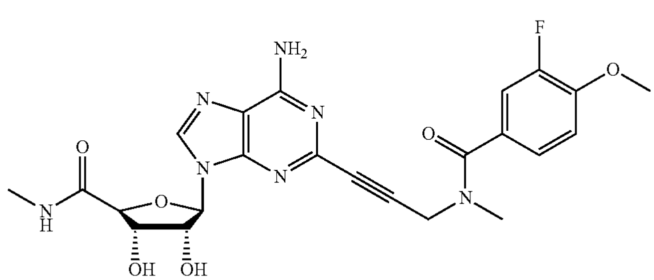 | 514.25 7.3 min | + |
| 30. | 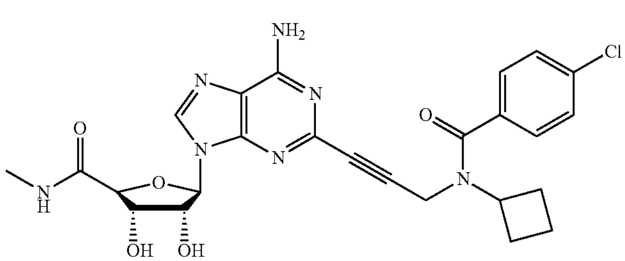 | 540.30 8.9 min | + |

TABLE 1-continued

| Ex # | Structure | LRMS ESI (M + H+) Ret. Time (RT) | Ki |
|---|---|---|---|
| 31. | 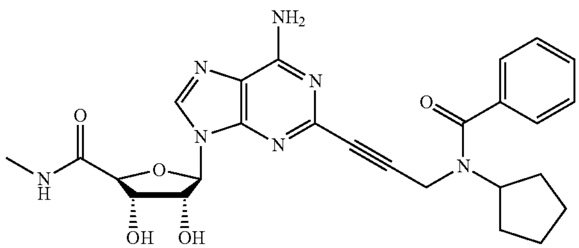 | 520.30<br>8.5 min | + |
| 32. | 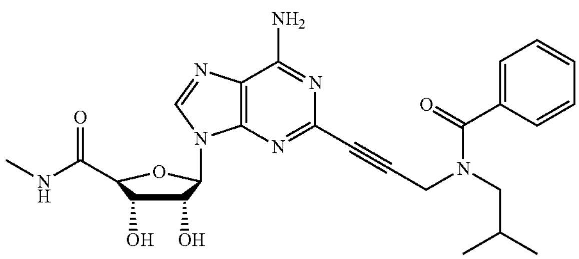 | 508.30<br>8.3 min | + |
| 33. | 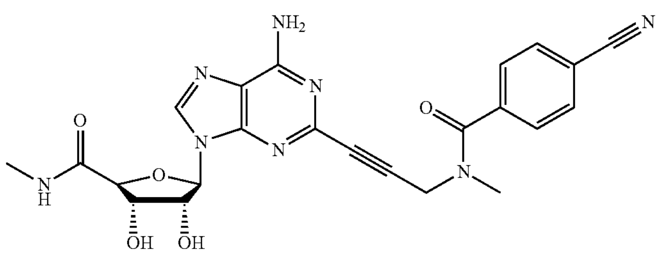 | 491.25<br>6.6 min | + |
| 34. | 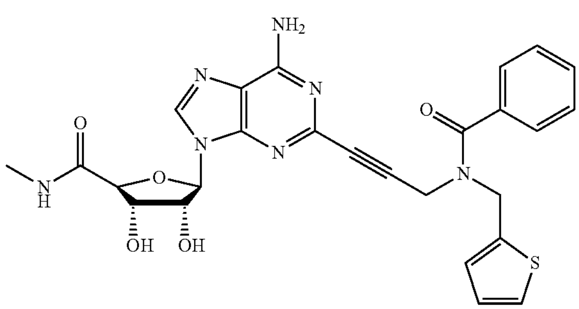 | 548.25<br>8.4 min | ++ |
| 35. | 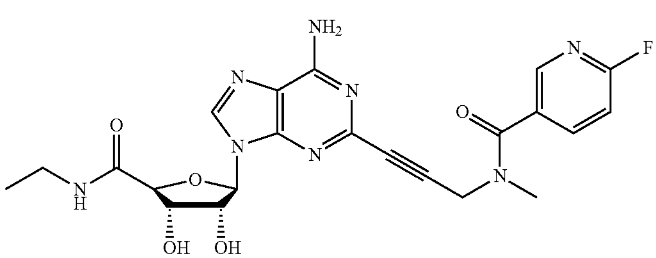 | 499.40<br>5.3 min | + |

TABLE 1-continued

| Ex # | Structure | LRMS ESI (M + H+) Ret. Time (RT) | Ki |
|---|---|---|---|
| 36. | 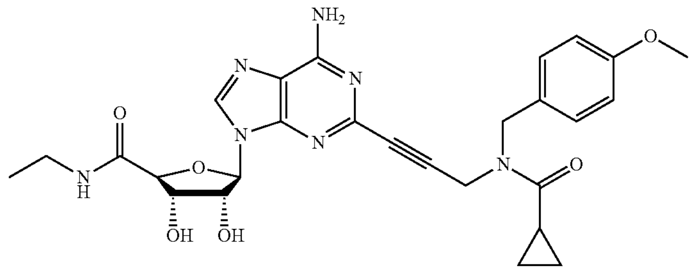 | 550.45 7.7 min | ++ |

+++ >50 nM
++ 1-50 nM
+ <1 nM

Examples 1-33 of Table 2 are additional representative examples of the present invention. These examples can be synthesized using the methods described above by coupling the corresponding methyl/ethyl/cyclopropyl-uronamide and corresponding 2-substituted-propyn-1-yl. The starting 2-substituted-propyn-1-yl groups can be prepared according to the general procedures provided above.

TABLE 2

| Ex. # | Structure |
|---|---|
| 1. | 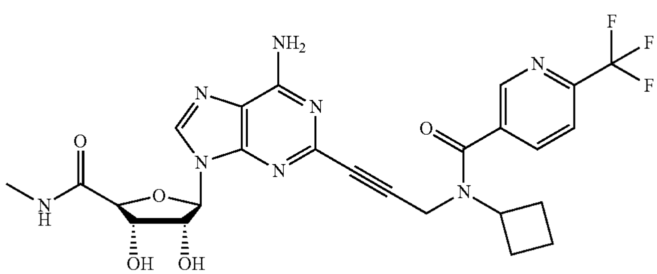 |
| 2. | 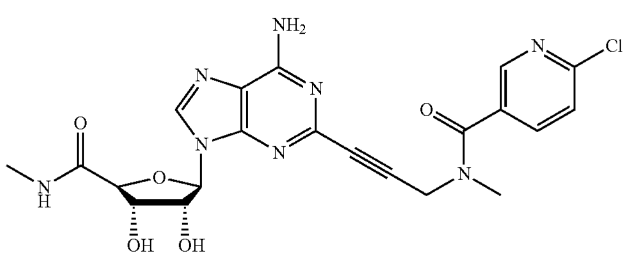 |
| 3. | 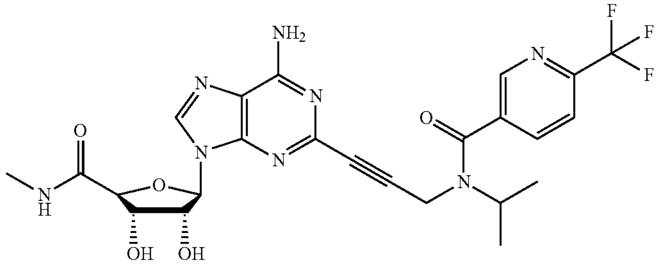 |

TABLE 2-continued
| Ex. # | Structure |
|---|---|
| 4. | 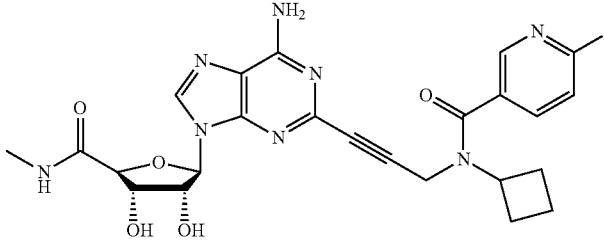 |
| 5. | 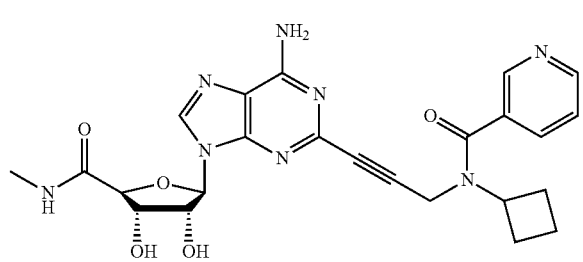 |
| 6. | 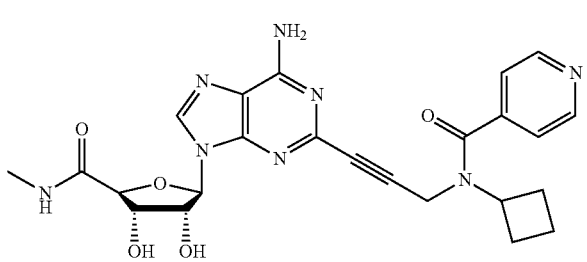 |
| 7. | 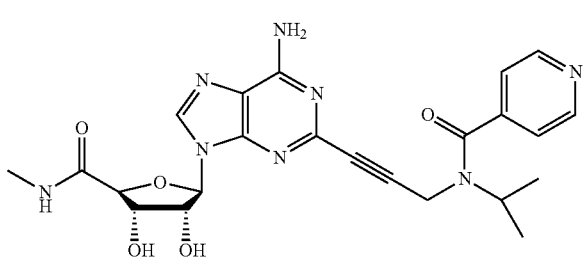 |
| 8. | 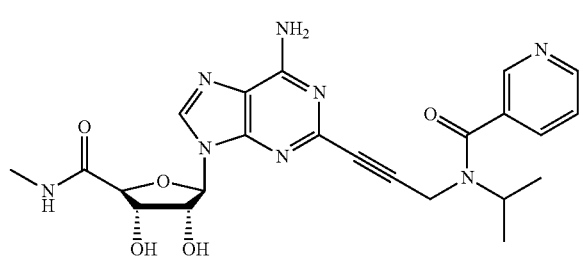 |
| 9. | 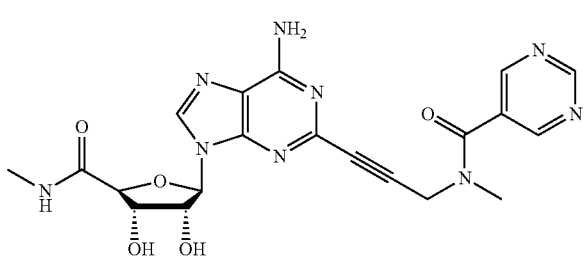 |

TABLE 2-continued

| Ex. # | Structure |
|---|---|
| 10. | 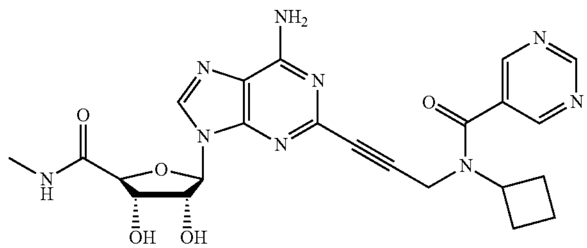 |
| 11. | 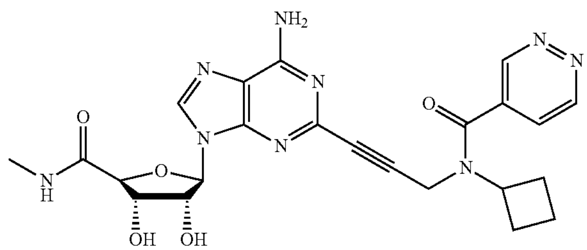 |
| 12. | 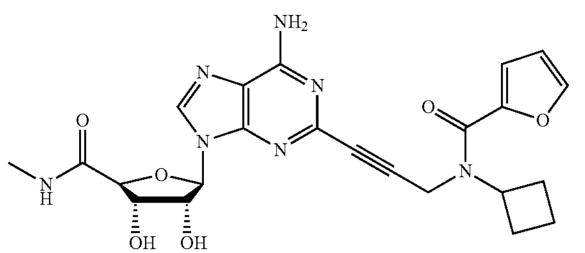 |
| 13. | 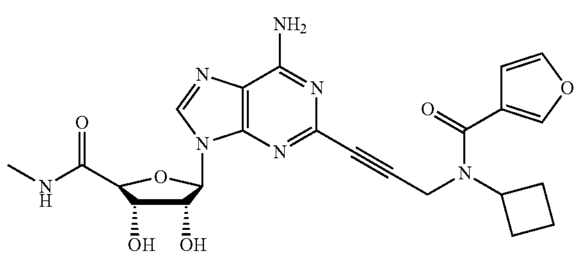 |
| 14. | 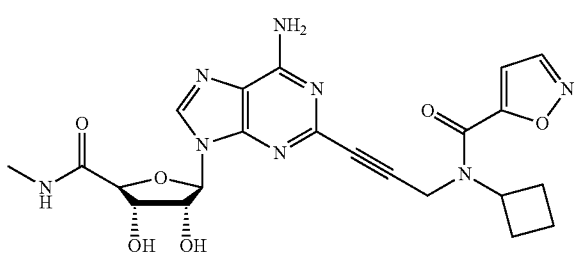 |
| 15. | 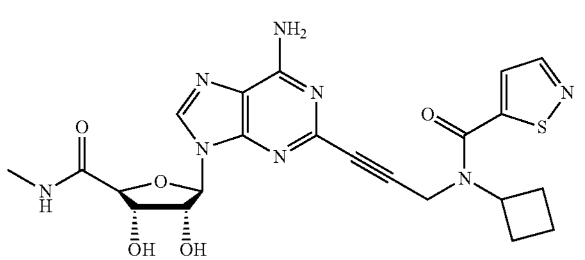 |

TABLE 2-continued

| Ex. # | Structure |
|---|---|
| 16. | 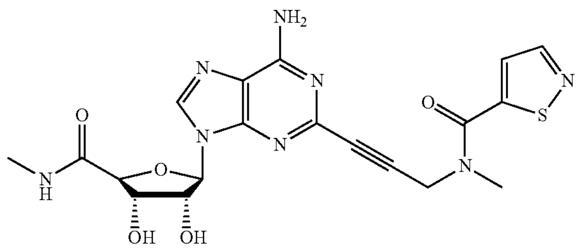 |
| 17. | 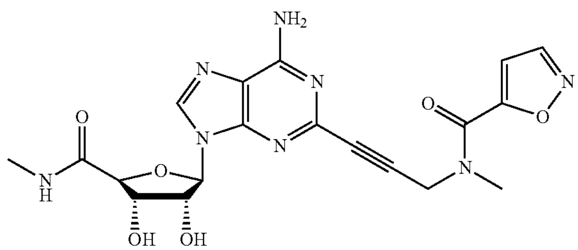 |
| 18. | 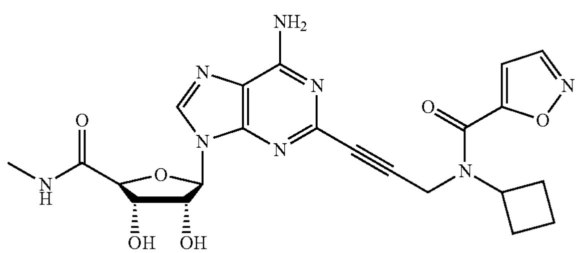 |
| 19. | 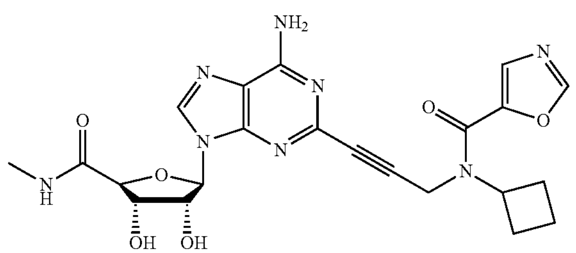 |
| 20. | 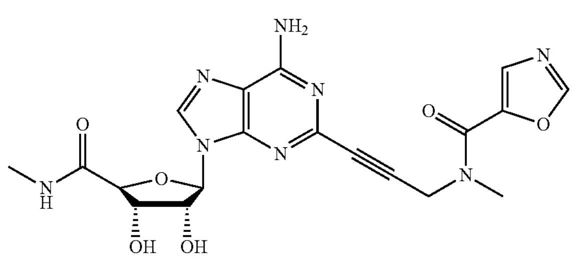 |
| 21. | 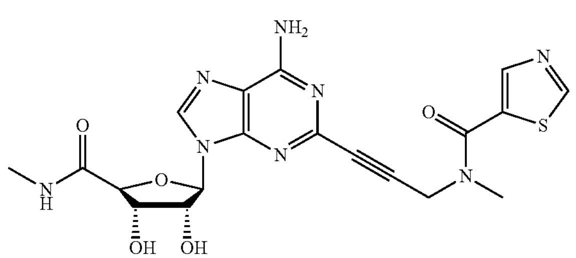 |

TABLE 2-continued

| Ex. # | Structure |
|---|---|
| 22. | 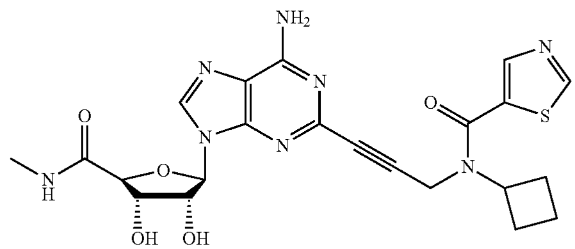 |
| 23. | 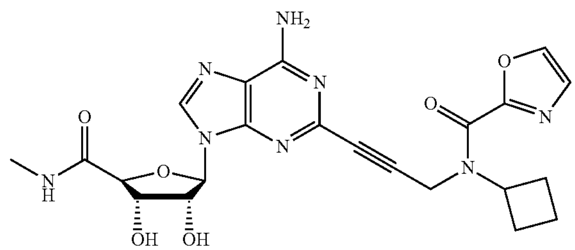 |
| 24. | 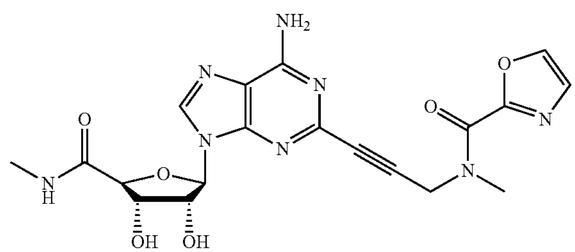 |
| 25. | 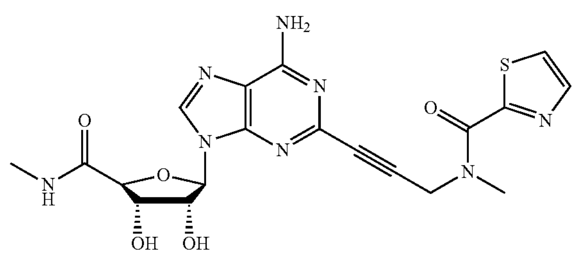 |
| 26. | 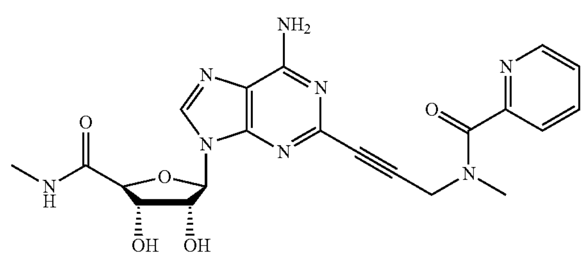 |
| 27. | 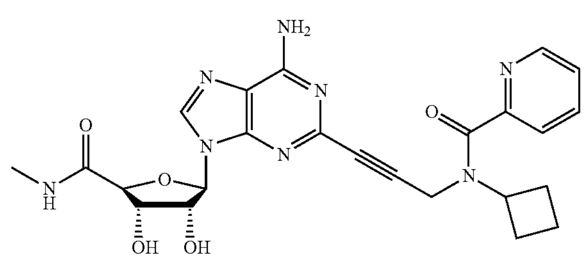 |

TABLE 2-continued

| Ex. # | Structure |
|---|---|
| 28. | 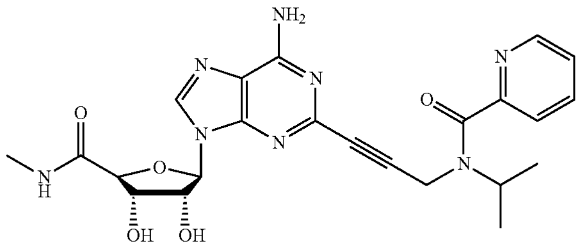 |
| 29. | 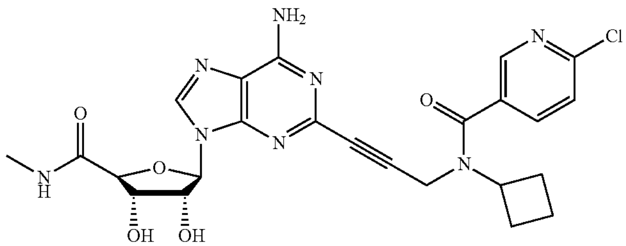 |
| 30. | 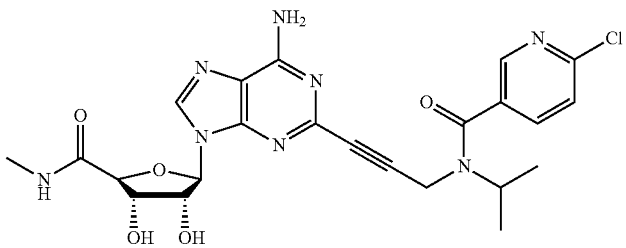 |
| 31. | 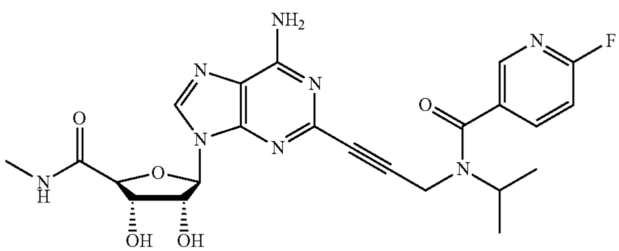 |
| 32. | 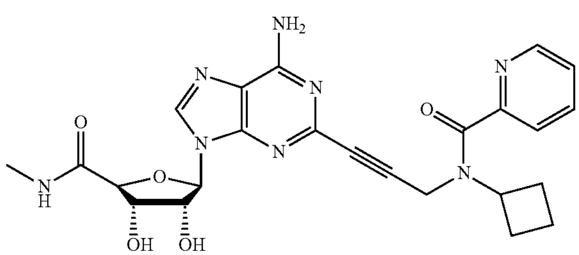 |
| 33. | 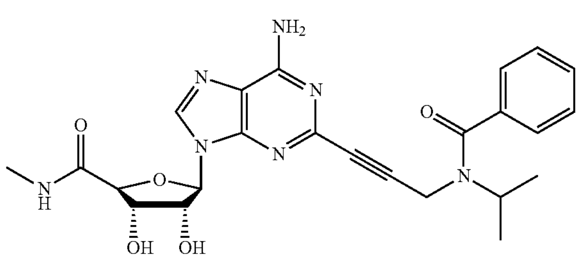 |

All references listed herein are individually incorporated in their entirety by reference.

Numerous modifications and variations of the present invention are possible in light of the above teachings. It is therefore to be understood that within the scope of the appended claims, the invention may be practiced otherwise than as specifically described herein.

What is claimed is:

1. A compound of Formula Ia or a stereoisomer or pharmaceutically acceptable salt thereof:

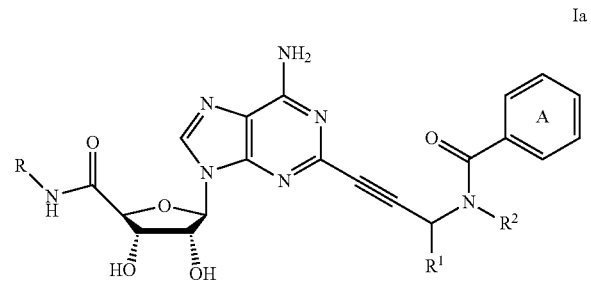

wherein:
R is $CH_3$;
$R^1$ is independently selected from: H, $C_{1-8}$ alkyl, and $C_{3-8}$ cycloalkyl;
$R^2$ is selected from: H, $C_{1-8}$ alkyl-$C_{3-8}$ cycloalkyl, $C_{3-8}$cycloalkyl-$C_{1-8}$ alkylene-, $C_{1-8}$ alkoxy-$C_{1-8}$ alkylene-, 5-10 membered heterocyclyl, 5-10 membered heterocyclyl-$C_{1-8}$ alkylene-, 5-10 membered heteroaryl, 5-10 membered heteroaryl-$C_{1-8}$ alkylene-, aryl, and aryl-$C_{1-8}$ alkylene-;
ring A is a phenyl ring or a 5-6 membered heteroaryl attached via the carbon atom shown and having 1-3 ring heteroatoms selected from O, N, and $S(O)_p$;
ring A is optionally substituted with 1-3 $R^3$ groups;
$R^3$ is independently selected from: $C_{1-8}$ alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, $OC(O)R^a$, $OCO_2R^a$, $OC(O)NR^aR^b$, $NR^b\text{-}COR^a$, $NR^bCO_2R^a$, $NR^bC(O)NR^aR^b$, $S(O)_pNR^aR^b$, $C_{3-10}$cycloalkyl, $C_{3-10}$cycloalkyl-$C_{1-8}$alkylene-, 5-10 membered heterocyclyl, 5-10 membered heterocyclyl-$C_{1-8}$alkylene-, aryloxy, aryl, aryl-, -$C_{1-8}$alkylene-, 5-10 membered heteroaryl, and 5-10 membered heteroaryl-$C_{1-8}$alkylene-;
$R^a$ is independently selected from: H, $C_{1-8}$ alkyl, $C_{3-8}$cycloalkyl, and $C_{3-8}$ $C_{1-8}$ alkylene-; and,
$R^b$ is independently selected from: H, $C_{1-8}$ alkyl, $C_{3-8}$ cycloalkyl, and $C_{3-8}$ cycloalkyl-$C_{1-8}$ alkylene-.

2. A compound of claim 1, or a stereoisomer or pharmaceutically acceptable salt thereof, wherein:
R is $CH_3$;
$R^1$ is selected from: H and $C_{1-4}$ alkyl;
$R^2$ is selected from: H, $C_{1-4}$ alkyl, $C_{3-6}$ cycloalkyl, $C_{3-6}$ cycloalkyl-$C_{1-2}$alkylene-, and $C_{1-4}$alkoxy-$C_{1-4}$ alkylene-;
ring A is selected from phenyl, pyridyl, thienyl, furanyl, pyrrolyl, oxazolyl, isoxazolyl, thiazolyl, isothiazolyl, pyrimidyl, and pyridazinyl;
ring A is optionally substituted with 1-2 $R^3$ groups;
$R^3$ is independently selected from: $C_{1-4}$alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;
$R^a$ is independently selected from: H, $C_{1-4}$alkyl and $C_{3-8}$cycloalkyl, and $C_{3-8}$cycloalkyl-$C_{1-8}$ alkylene-;
$R^b$ is independently selected from: H, $C_{1-4}$alkyl, $C_{3-8}$ cycloalkyl, and $C_{3-8}$ cycloalkyl-$C_{1-8}$ alkylene-; and,
p is independently selected from: 0, 1, and 2.

3. A compound of claim 2, or a stereoisomer or pharmaceutically acceptable salt thereof, wherein:
R is methyl;
$R^1$ is H;
$R^2$ is selected from: H, methyl, ethyl, isopropyl, isobutyl, cyclopropyl, cyclopropyl-methylene, cyclobutyl, cyclobutyl-methylene, cyclopentyl, and methoxy-ethylene;
ring A is selected from: phenyl, pyridyl, and thienyl;
ring A is optionally substituted with 1-2 $R^3$ groups;
$R^3$ is independently selected from: $C_{1-4}$alkyl, F, Cl, Br, I, —CN, $OR^a$, $SR^a$, $NR^aR^b$, $CF_3$, $OCF_3$, $COR^a$, $CO_2R^a$, $C(O)NR^aR^b$, and $S(O)_pNR^aR^b$;
$R^a$ is independently selected from: H and $C_{1-4}$alkyl;
$R^b$ is independently selected from: H and $C_{1-4}$alkyl; and,
p is independently selected from: 0, 1, and 2.

4. A compound of claim 3, or a stereoisomer or pharmaceutically acceptable salt thereof, wherein:
R is methyl;
$R^1$ is H;
$R^2$ is selected from: methyl, isobutyl, cyclopropyl, cyclopropyl-methylene, cyclobutyl, cyclopentyl, and methoxy-ethylene;
ring A is selected from: phenyl, pyridyl, and thienyl;
ring A is optionally substituted with 1-2 $R^3$ groups;
$R^3$ is independently selected from: $C_{1-4}$alkyl, F, Cl, —CN, $OR^a$, $CF_3$, and $OCF_3$;
$R^a$ is independently selected from: H and $C_{1-4}$alkyl; and,
$R^b$ is independently selected from: H and $C_{1-4}$alkyl.

5. A compound of claim 4, or a stereoisomer or pharmaceutically acceptable salt thereof, wherein:
R is methyl;
$R^1$ is H;
$R^2$ is selected from: methyl, isobutyl, cyclopropyl, cyclopropyl-methylene, cyclobutyl, cyclopentyl, and methoxy-ethylene;
ring A is phenyl optionally substituted with 1-2 $R^3$ groups; and,
$R^3$ is independently selected from: $CH_3$, F, Cl, —CN, $CF_3$, and $OCF_3$.

6. A compound of claim 4, or a stereoisomer or pharmaceutically acceptable salt thereof, wherein:
R is methyl;
$R^1$ is H;
$R^2$ is selected from: methyl, isobutyl, cyclopropyl, cyclopropyl-methylene, cyclobutyl, cyclopentyl, and methoxy-ethylene;
ring A is 3-pyridyl optionally substituted with 1-2 $R^3$ groups; and,
$R^3$ is independently selected from: $CH_3$, F, Cl, —CN, $CF_3$, and $OCF_3$.

7. A compound of claim 4, or a stereoisomer or pharmaceutically acceptable salt thereof, wherein:
R is methyl;
$R^1$ is H;
$R^2$ is selected from: methyl, isobutyl, cyclopropyl, cyclopropyl-methylene, cyclobutyl, cyclopentyl, and methoxy-ethylene;
ring A is 4-pyridyl optionally substituted with 1-2 $R^3$ groups; and,
$R^3$ is independently selected from: $CH_3$, F, Cl, —CN, $CF_3$, and $OCF_3$.

8. A compound of claim 4, or a stereoisomer or pharmaceutically acceptable salt thereof, wherein:

R is methyl;
R¹ is H;
R² is selected from: methyl, isobutyl, cyclopropyl, cyclopropyl-methylene, cyclobutyl, cyclopentyl, and methoxy-ethylene;
ring A is 2-thienyl optionally substituted with 1-2 R³ groups; and, R³ is independently selected from: $CH_3$, F, Cl, —CN, $CF_3$, and $OCF_3$.

9. A compound of claim 1, or a stereoisomer or pharmaceutically acceptable salt thereof, wherein the compound is selected from compounds 1-20 as follows:

1. 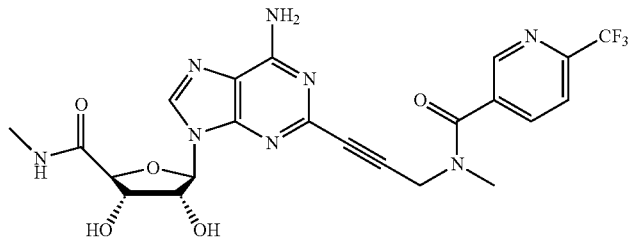

2. 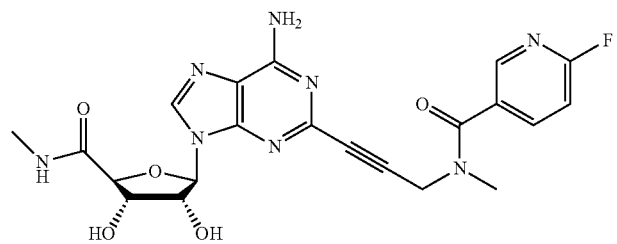

3. 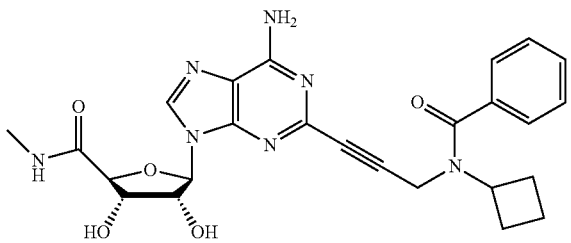

4. 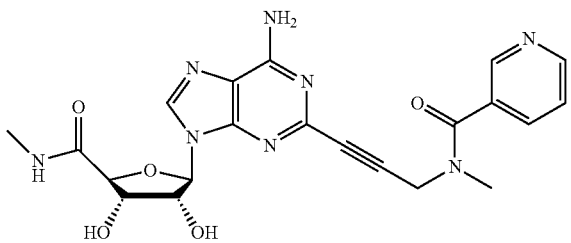

5. 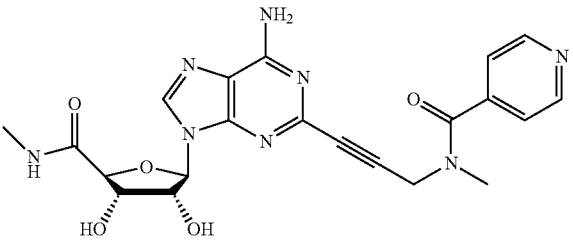

6. 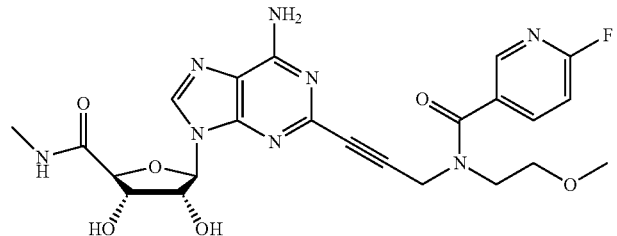

7. 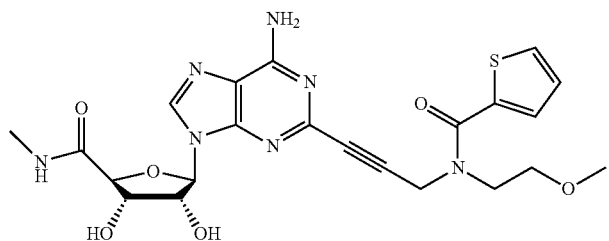
8. 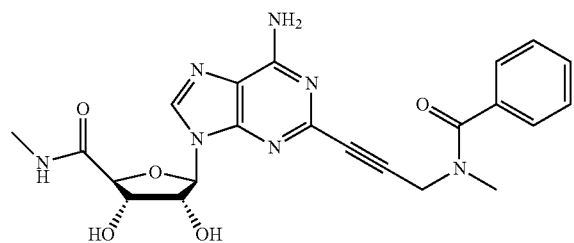
9. 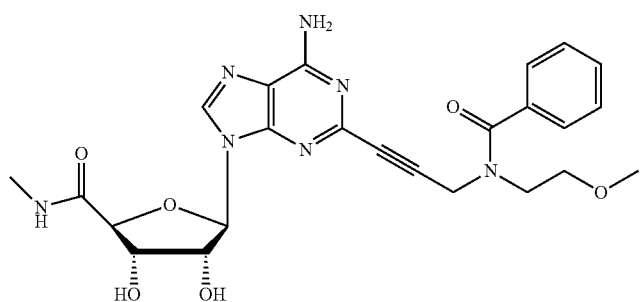
10. 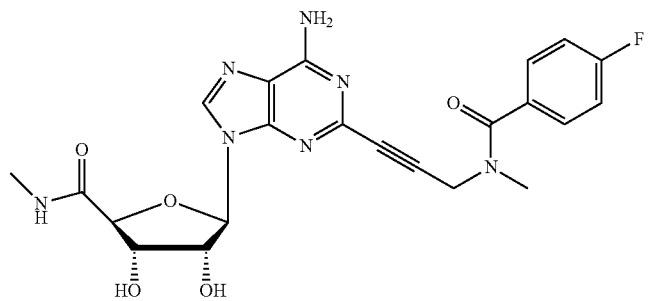
11. 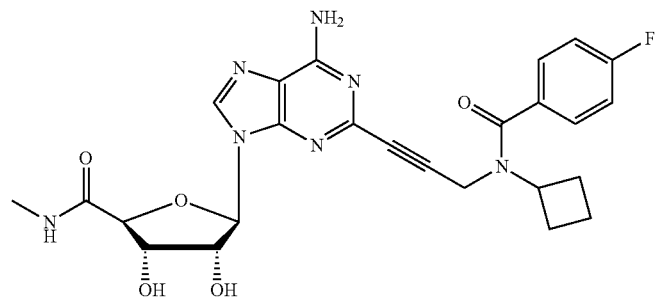

12. 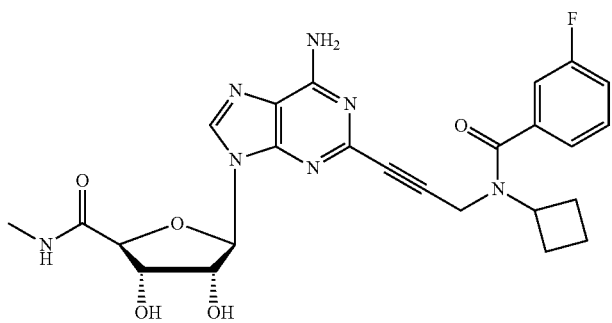
13. 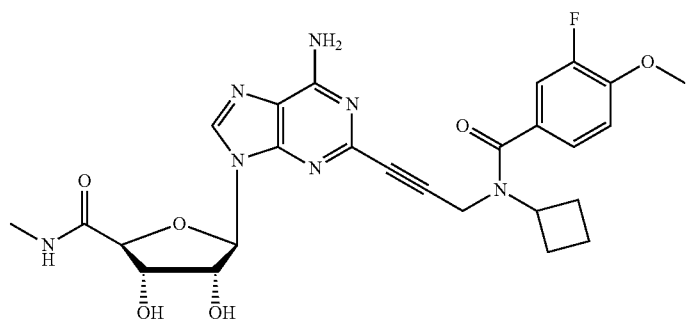
14. 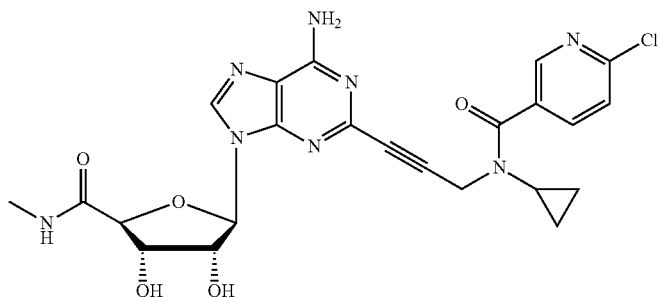
15. 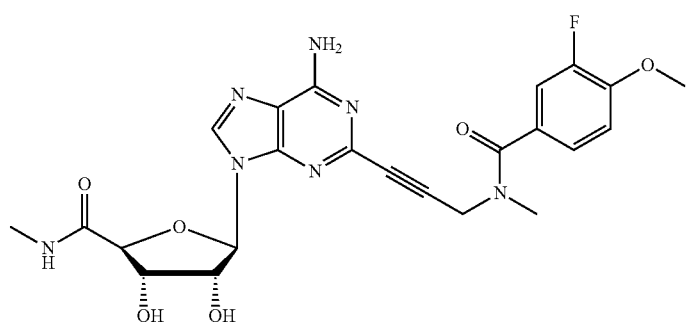
16. 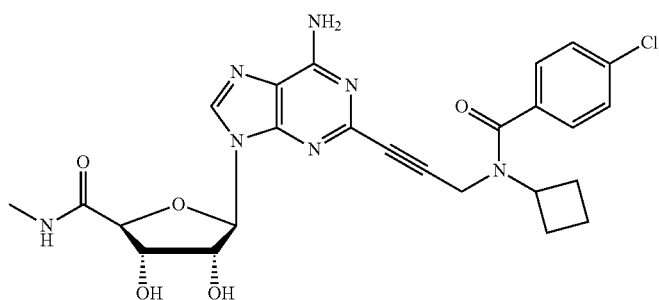

-continued
17.
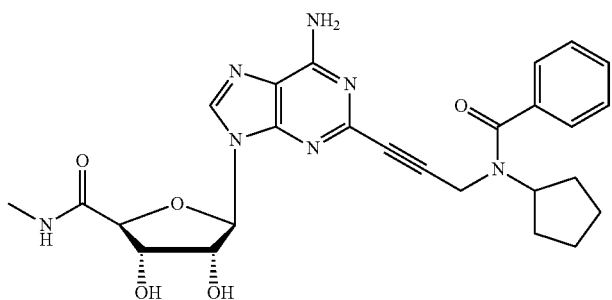
18.
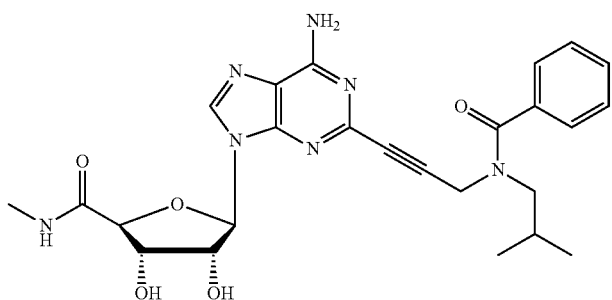
19.
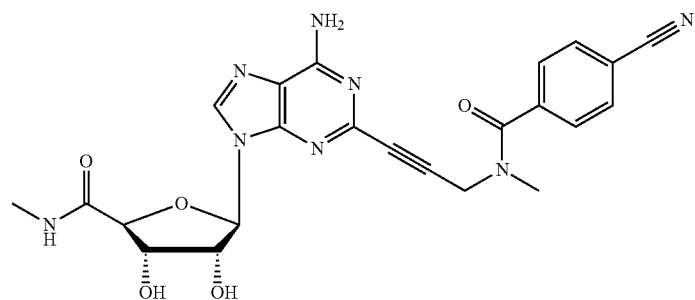
20.
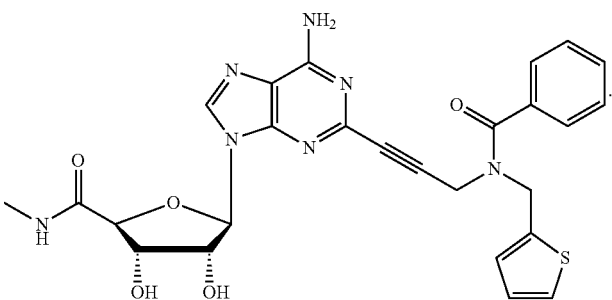

10. A compound of claim 9, wherein the compound is selected from:

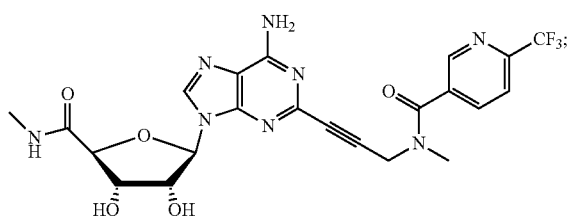

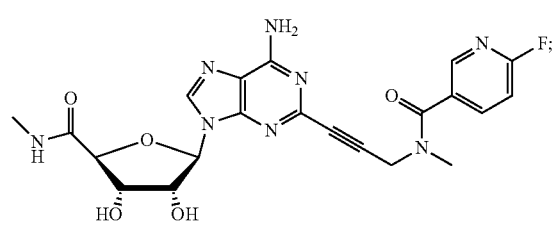

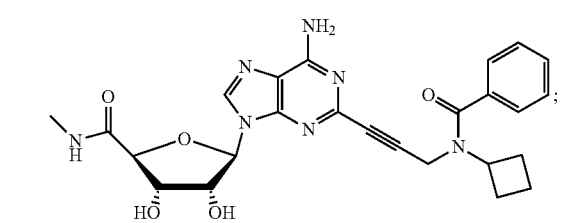

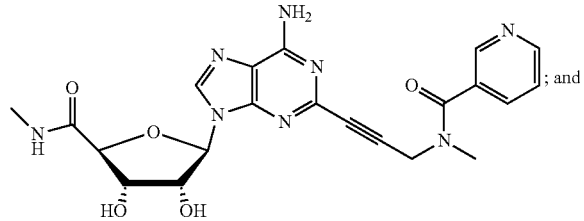; and

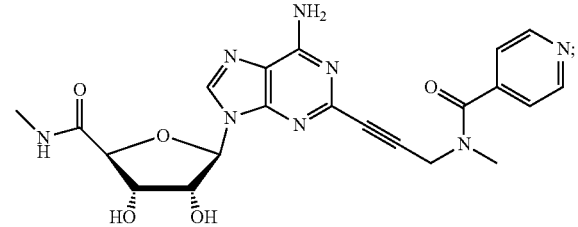

or a stereoisomer or pharmaceutically acceptable salt thereof.

11. A pharmaceutical composition, comprising: a therapeutically effective amount of a compound of claim 1 or a stereoisomer or pharmaceutically acceptable salt thereof and a pharmaceutically acceptable carrier.

12. A method for treating an adenosine $A_{2A}$ receptor associated state in a subject, comprising: administering to the subject an effective amount of a compound of claim 1 or a stereoisomer or pharmaceutically acceptable salt thereof.

13. The method of claim 12, wherein the adenosine $A_{2A}$ receptor associated state is selected from an autoimmune stimulation, inflammation, allergic diseases, skin diseases, infectious diseases, wasting diseases, organ transplantation, tissue or cell transplantation, neuropathic pain, open wounds, adverse effects from drug therapy, a cardiovascular condition, ischemia-reperfusion injury, dialysis, gout, chemical trauma, thermal trauma, diabetic nephropathy, sickle cell disease, laminitis, founder's disease, glaucoma, and ocular hypertension, spinal injury, myocardial infarction, acute myocardial infarction.

14. The method of claim 12, wherein the adenosine $A_{2A}$ receptor associated state is selected from: arthritis, Crohn's disease, chronic obstructive pulmonary disease, sepsis, inflammatory bowel disease, glaucoma, ocular hypertension, diabetic nephropathy, tissue or cell transplantation.

15. The method of claim 12, wherein the adenosine $A_{2A}$ receptor associated state is caused by Shiga toxin, *Clostridium difficile*, or *Clostridium difficile* toxin A-induced condition.

16. A method of diagnosing myocardial perfusion abnormalities in a mammal, comprising:

a. parenterally administering to the mammal a unit dose of a compound of claim 1; and, b. performing a technique on the mammal to detect the presence of coronary artery stenosis, assess the severity of coronary artery stenosis, or a combination therof.

17. A method of reducing interocular pressure in a subject, comprising: administering to the subject an effective amount of a compound of claim 1 or a stereoisomer or pharmaceutically acceptable salt thereof, such that the intraocular pressure is reduced.

18. A compound of claim 1, or a stereoisomer or pharmaceutically acceptable salt thereof, wherein the compound is selected from compounds 1-33 as follows:

| Ex. # | Structure |
|---|---|
| 1. | 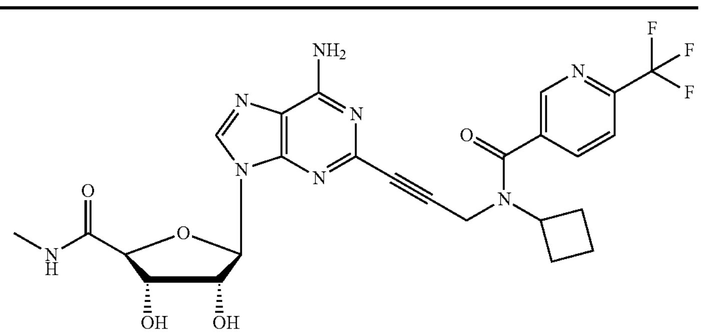 |

-continued

| Ex. # | Structure |
|---|---|
| 2. | 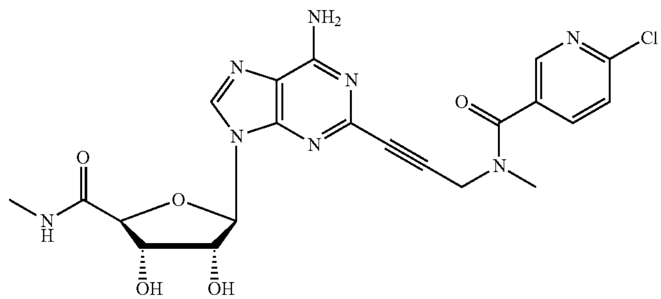 |
| 3. | 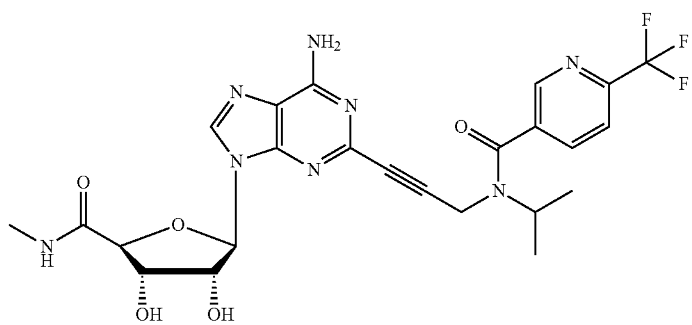 |
| 4. | 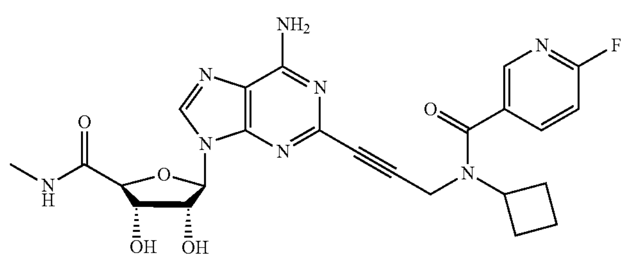 |
| 5. | 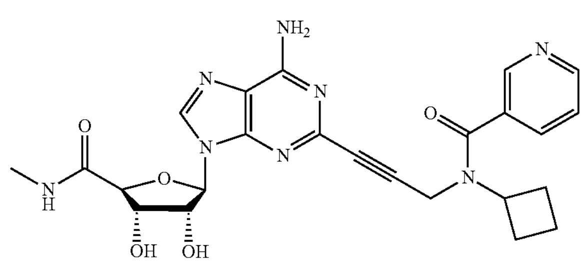 |
| 6. | 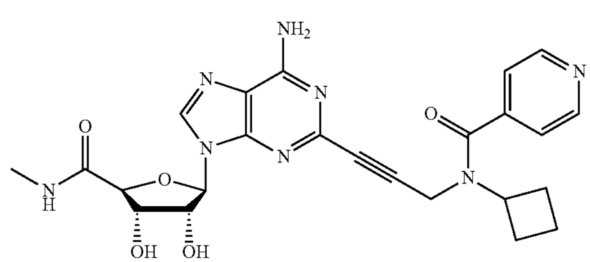 |

-continued
| Ex. # | Structure |
|---|---|
| 7. | 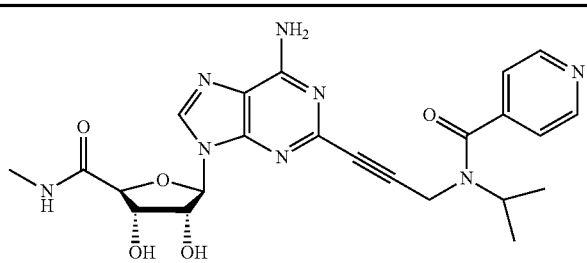 |
| 8. | 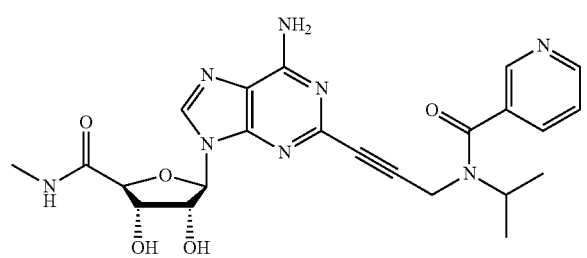 |
| 9. | 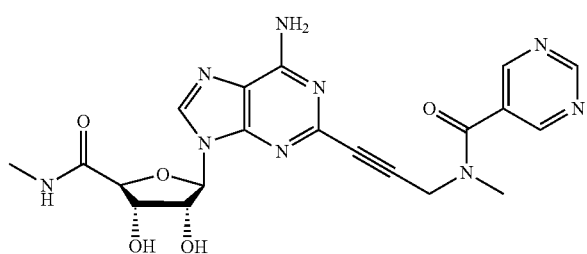 |
| 10. | 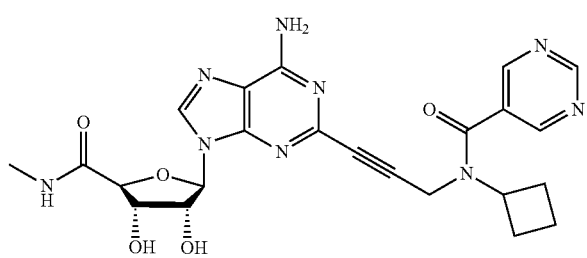 |
| 11. | 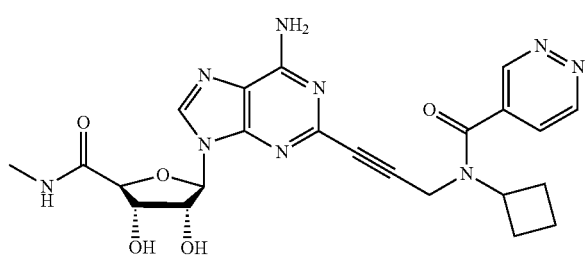 |
| 12. | 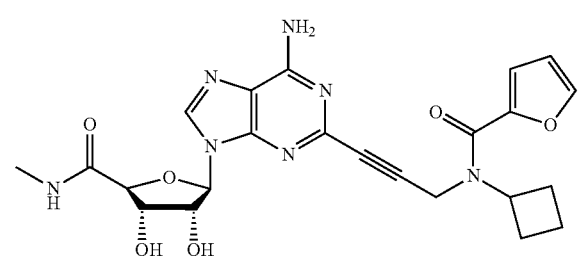 |

| Ex. # | Structure |
|---|---|
| 13. | 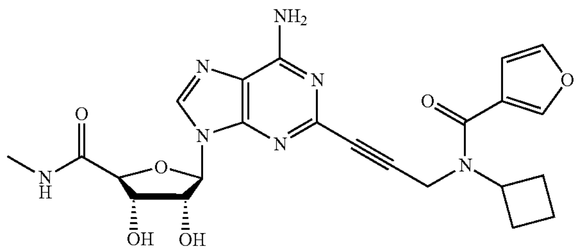 |
| 14. | 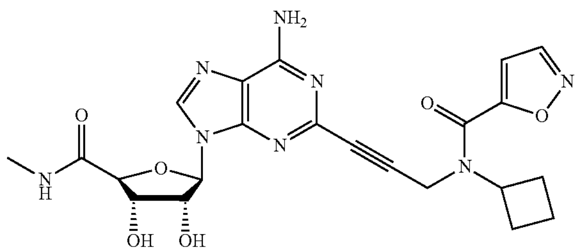 |
| 15. | 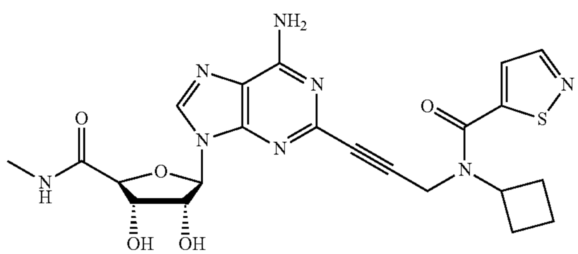 |
| 16. | 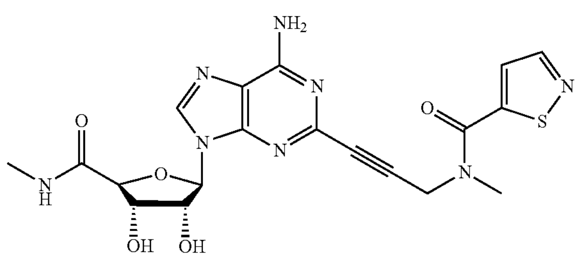 |
| 17. | 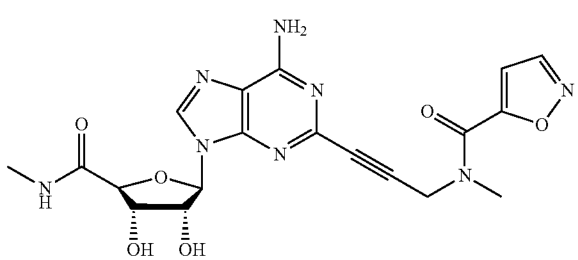 |
| 18. | 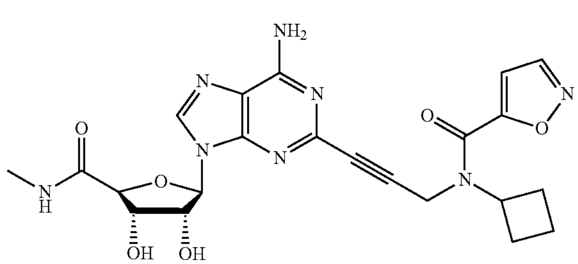 |

| Ex. # | Structure |
|---|---|
| 19. | 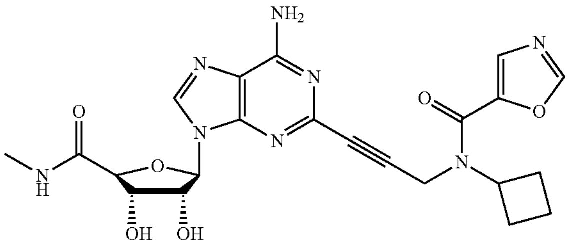 |
| 20. | 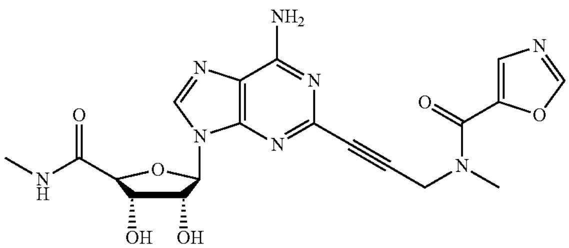 |
| 21. | 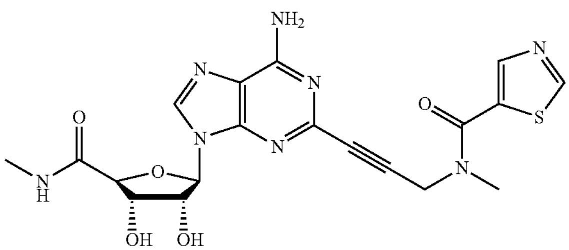 |
| 22. | 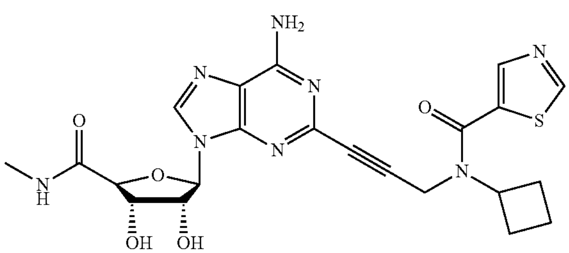 |
| 23. | 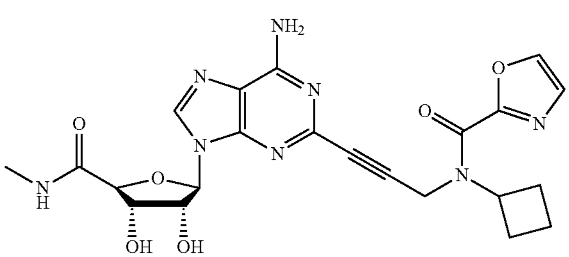 |
| 24. | 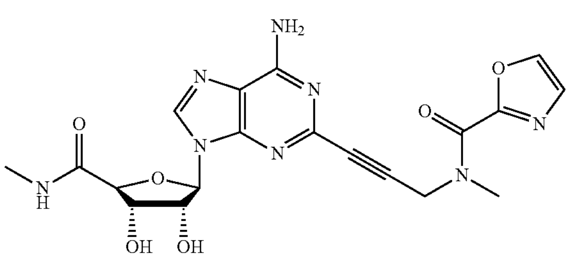 |

| Ex. # | Structure |
|---|---|
| 25. | (structure) |
| 26. | (structure) |
| 27. | (structure) |
| 28. | (structure) |
| 29. | (structure) |
| 30. | (structure) |

-continued
| Ex. # | Structure |
|---|---|
| 31. | 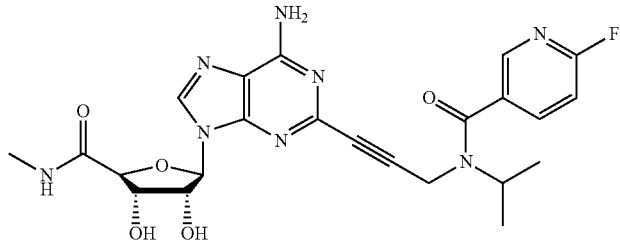 |
| 32. | 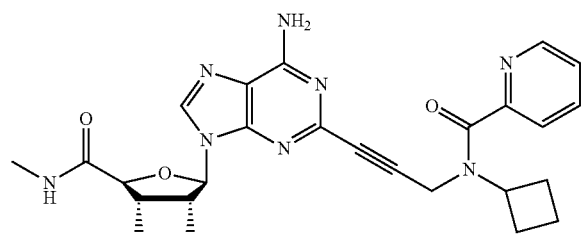 |
| 33. | 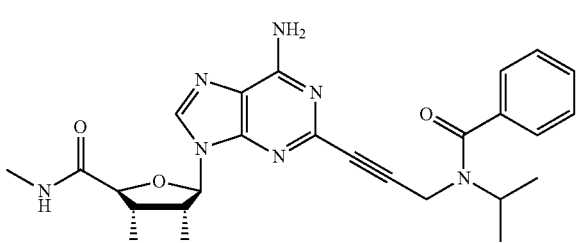 |
* * * * *